(12) United States Patent
Cheng et al.

(10) Patent No.: US 7,091,031 B2
(45) Date of Patent: Aug. 15, 2006

(54) CAROTENOID HYDROXYLASE ENZYMES

(75) Inventors: Qiong Cheng, Wilmington, DE (US); Luan Tao, Havertown, PA (US); Natalia Sedkova, Cherry Hill, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/200,394

(22) Filed: Aug. 9, 2005

(65) Prior Publication Data

US 2006/0035312 A1   Feb. 16, 2006

Related U.S. Application Data

(60) Provisional application No. 60/601,947, filed on Aug. 16, 2004.

(51) Int. Cl.
C12N 1/21 (2006.01)
C12N 1/13 (2006.01)
C12N 1/15 (2006.01)
C12N 1/19 (2006.01)
C12N 5/10 (2006.01)
C12N 15/63 (2006.01)
C12N 9/02 (2006.01)

(52) U.S. Cl. ............ 435/252.3; 435/189; 435/320.1; 435/254.1; 435/255.1; 435/419; 435/411; 435/412; 435/414; 435/415; 435/252.1; 435/252.31; 435/252.32; 435/252.33; 435/252.34; 435/252.35; 435/254.21; 435/254.22; 435/254.23; 435/254.3; 435/254.6; 435/257.2; 536/23.2

(58) Field of Classification Search ................ 435/183, 435/252.3, 23.2
See application file for complete search history.

(56) References Cited

U.S. PATENT DOCUMENTS

| | | | |
|---|---|---|---|
| 5,684,238 | A | 11/1997 | Ausich et al. |
| 5,811,273 | A | 9/1998 | Misawa et al. |
| 6,291,204 | B1 | 9/2001 | Pasamontes et al. |
| 6,677,134 | B1 | 1/2004 | Pasamontes et al. |
| 2002/0102631 | A1 | 8/2002 | Cunningham et al. |
| 2002/0147371 | A1 | 10/2002 | Hohmann et al. |

FOREIGN PATENT DOCUMENTS

| | | |
|---|---|---|
| CN | 1380415 | 4/2001 |
| EP | 0 393 690 B1 | 3/1995 |
| WO | WO 00/061764 A1 | 10/2000 |
| WO | WO 02/079395 A2 | 10/2002 |
| WO | WO 03/016503 A2 | 2/2003 |
| WO | WO 2004/029275 A1 | 4/2004 |
| WO | WO 2005/049643 A1 | 6/2005 |

OTHER PUBLICATIONS

Nelis et. al., Microbial Sources of Carotenoid Pigments Used in Foods and Feeds. Appl. Bacteriol., 1991, pp. 181-191, vol. 70.

Misawa et. al., Metabolic Engineering for the Production of Carotenoids in Non-Carotenogenic Bacteria and Yeasts, J. Biotech., 1998, pp. 169-181, vol. 59.

Misawa et. al., Elucidation of the Erwinia Uredovora Carotenoid Biosynthetic Pathway by Functional Analysis of Gene Products Expressed in *Escherichia coli*. J. Bacteriol., 1990, pp. 6704-6712, vol. 172.

Hundle et. al., Functional Assignment of Erwinia Herbicola Eho10 Carotenoid Genes Expressed in *Escherichia coli*, Mol. Gen. Genet., 1994, pp. 406-416, vol. 245.

Hundle et. al., In Vitro Expression and Activity of Lycopene Cyclase and B-Carotene Hydroxylase From Erwinia Herbicola, FEBS Lett., 1993, pp. 329-334, vol. 315.

Schnurr et. al., Mapping of a Carotenogenic Gene Cluster From Erwinia Herbicola and Functional Identification of Six Genes, FEMS Microbiol. Lett., 1991, pp. 157-161, vol. 78.

Misawa et. al., Structure and Functional Analysis of a Marine Bacterial Carotenoid Biosynthesis Gene Cluster and Astaxanthin Biosynthetic Pathway Proposed at the Gene Level. J. Bacteriol., 1995, pp. 6575-6584, vol. 177.

Pasamontes et. al., Isolation and Characterization of the Carotenoid Biosynthesis Genes of *Flavobacterium* sp. Strain R1534, Gene, 1997, pp. 35-41, vol. 185.

H. Linden, Carotenoid Hydroxylase From *Haematococcus Pluvialis*: CDNA Sequence, Regulation and Functional Complementation, Biochimicaet Biophysica Acta, 1999, pp. 203-212, vol. 1446.

L. Tian et. al., Characterization of a Second Carotenoid B-Hydroxylase Gene From Arabidopsis and its Relationship to the Luti Locus, Plant Mol. Biol., 2001, pp. 379-388, vol. 47.

Y. Nishida et. al., Elucidation of a Gene Cluster Encoding a Novel Carotenoid Biosynthetic Enzyme From *Brevundimonas* sp. SD212, 2,2'—Beta-Hydroxylase, and Combinatorial Biosynthesis of New or Rare Xanthophylls, Appl. Environ. Microbiol., 2005.

*Primary Examiner*—Rebecca E. Prouty
*Assistant Examiner*—Iqbal Chowdhury

(57) ABSTRACT

A novel CrtZ carotenoid hydroxylase, isolated from *Brevundimonas vesicularis* DC263, is provided that is useful for the production of hydroxylated carotenoids. Additionally, a previously identified hypothetical protein from *Novosphingobium aromaticivorans* has found to have carotenoid hydroxylase activity. Both hydroxylase genes exhibit low homology in comparison to other CrtZ hydroxylases previously reported. Expression of the hydroxylases in heterologous host cells enabled production of hydroxylated carotenoids.

7 Claims, 5 Drawing Sheets

SEQUENCE LISTING

<160> NUMBER OF SEQ ID NOS: 38

<210> SEQ ID NO 1
<211> LENGTH: 19
<212> TYPE: DNA
<213> ORGANISM: Artificial sequence
<220> FEATURE:
<223> OTHER INFORMATION: primer

<400> SEQUENCE: 1
gagtttgatc ctggctcag                                                  19

<210> SEQ ID NO 2
<211> LENGTH: 15
<212> TYPE: DNA
<213> ORGANISM: Artificial sequence
<220> FEATURE:
<223> OTHER INFORMATION: primer

<400> SEQUENCE: 2
acgggcggtg tgtac                                                      15

<210> SEQ ID NO 3
<211> LENGTH: 16
<212> TYPE: DNA
<213> ORGANISM: Artificial sequence
<220> FEATURE:
<223> OTHER INFORMATION: primer

<400> SEQUENCE: 3
gccagcagcc gcggta                                                     16

<210> SEQ ID NO 4
<211> LENGTH: 1268
<212> TYPE: DNA
<213> ORGANISM: Brevundimonas vesicularis DC263

<400> SEQUENCE: 4
acgctggcgg caggcctaac acatgcaagt cgaacgaact cttcggagtt agtggcggac      60
gggtgagtaa cacgtgggaa cgtgccttta ggttcggaat aactcaggga aacttgtgct     120
aataccgaat gtgcccttcg ggggaaagat ttatcgcctt tagagcggcc cgcgtctgat     180
tagctagttg gtgaggtaaa ggctcaccaa ggcgacgatc agtagctggt ctgagaggat     240
gatcagccac attgggactg agacacggcc caaactccta cgggaggcag cagtggggaa     300
tcttgcgcaa tgggcgaaag cctgacgcag ccatgccgcg tgaatgatga aggtcttagg     360
attgtaaaat tctttcaccg gggacgataa tgacggtacc cggagaagaa gccccggcta     420
acttcgtgcc agcagccgcg gtaatacgaa ggggctagc gttgctcgga attactgggc      480
gtaaagggag cgtaggcgga catttaagtc agggtgaaa tcccgggct caacctcgga       540 attgcctttg atactgggtg tcttgagtat gagagaggtg tgtggaactc cgagtgtaga     600
ggtgaaattc gtagatattc ggaagaacac cagtggcgaa ggcgacacac tggctcatta     660
ctgacgctga ggctcgaaag cgtggggagc aaacaggatt agataccctg gtagtccacg     720
ccgtaaacga tgattgctag ttgtcgggat gcatgcattt cggtgacgca gctaacgcat     780
taagcaatcc gcctggggag tacggtcgca agattaaaac tcaaaggaat tgacggggc      840 ccgcacaagc ggtggagcat gtggtttaat tcgaagcaac gcgcagaacc ttaccacctt    900
ttgacatgcc tggaccgcca cggagacgtg gctttccctt cggggactag gacacaggtg    960

-continued

```
ctgcatggct gtcgtcagct cgtgtcgtga gatgttgggt taagtcccgc aacgagcgca    1020
accctcgcca ttagttgcca tcatttagtt gggaactcta atgggactgc cggtgctaag    1080
ccggaggaag gtgggatga cgtcaagtcc tcatggccct acagggtgg gctacacacg      1140 tgctacaatg gcgactacag agggttaatc cttaaaagtc gtctcagttc ggattgtcct    1200
ctgcaactcg aggcatgaa gttggaatcg ctagtaatcg cggatcagca tgccgcgggt     1260
gaatacgt                                                             1268
```

<210> SEQ ID NO 5
<211> LENGTH: 1291
<212> TYPE: DNA
<213> ORGANISM: Sphingomonas melonis DC18

<400> SEQUENCE: 5

```
acgctggcgg catgcctaac acatgcaagt cgaacgagat cttcgggtct agtggcgcac    60
gggtgcgtaa cgcgtgggaa tctgccccct tggttcggaat aaccgttgga aacgacggct   120
aataccggat gacgacgtaa gtccaaagat ttatcgccga gggatgagcc cgcgtaggat    180
tagctagttg gtgtggtaaa ggcgcaccaa ggcgacgatc cttagctggt ctgagaggat    240
gatcagccac actgggactg agacacggcc cagactccta cgggaggcag cagtggggaa    300
tattggacaa tgggcgcaag cctgatccag caatgccgcg tgagtgatga aggccttagg    360
gttgtaaagc tcttttaccc gggatgataa tgacagtacc gggagaataa gctccggcta    420
actccgtgcc agcagccgcg gtaatacgga gggagctagc gttgttcgga attactgggc    480
gtaaagcgca cgtaggcggc tttgtaagtt agaggtgaaa gcctggagct caactccaga    540
attgccttta agactgcatc gcttgaatcc aggagaggtg agtggaattc cgagtgtaga    600
ggtgaaattc gtagatattc ggaagaacac cagtggcgaa ggcggctcac tggactggta    660
ttgacgctga ggtgcgaaag cgtggggagc aaacaggatt agataccctg gtagtccacg    720
ccgtaaacga tgataactag ctgtccgggg acttggtctt gggtggcgc agctaacgca     780 ttaagttatc cgcctgggga gtacggccgc aaggttaaaa ctcaaatgaa ttgacggggg    840
cctgcacaag cggtggagca tgtggtttaa ttcgaagcaa cgcgcagaac cttaccagcg    900
tttgacatgt ccgacgatt tccagagatg gatctctttc cttcgggaac tggaacacag     960
gtgctgcatg gctgtcgtca gctcgtgtcg tgagatgttg ggttaagtcc cgcaacgagc    1020
gcaaccctcg cctttagtta ccatcattca gttggggact ctaaaggaac cgccggtgat    1080
aagccggagg aaggtgggga tgacgtcaag tcctcatggc ccttacgcgc tgggctacac    1140
acgtgctaca atggcggtga cagtgggcag caagcacgcg agtgtgcgct aatctccaaa    1200
agccgtctca gttcggattg cactctgcaa ctcgagtgca tgaaggcgga atcgctagta    1260
atcgcggatc agcatgccgc ggtgaatacg t                                   1291
```

<210> SEQ ID NO 6
<211> LENGTH: 6999
<212> TYPE: DNA
<213> ORGANISM: Enterobacteriaceae DC260

<400> SEQUENCE: 6

```
gcgatggcaa tggaaaatgt tgcgtgagct tttcgtctaa ctgcggcatc agcggctgaa    60
taatcagcac ggcaggtttg gtattcgtca ttttattgtc cattagcggt atttatttac    120
caccagccta acggagttat ttatgttacg gcgttgctgt tacttatttc gctaataaga    180
```

| | |
|---|---|
| tcacgcatag cattattaac aatatttacc tggtgcgcat gaatacgcac cctacaaagt | 240 |
| caagtccctc gctggcgaac tcaccttacg cagtctacgt ttaatcaaaa agcataaaaa | 300 |
| tttcaccaac catggatagc cattatgacc acccatgtcg acaccacagc acatcagaca | 360 |
| agcgaactcc ttcagctgca gcaaatttta caggcgcatc ttgaacattt actgcctgcc | 420 |
| ggacagcaaa gcgatcgcgt gcgtgccgcg atgcgtgccg aacgctggc gcagggcaaa | 480 |
| cgtattcgtc ctttattact gctgctgca gcgcgcgata tgggttgcga gctgacgcaa | 540 |
| aatggcgttc tcgatctcgc ctgtgcagtg gaaatggtgc acgcggcatc gctgattctg | 600 |
| gatgacattc cctcgatgga taacgcgcag atgcgtcgtg tcgccctac cgtgcatcgc | 660 |
| gaatttggtg aaaacgtggc gattctcgcc gccatcgcgc tgcttagccg cgcatttgaa | 720 |
| gtgattgcca ttgcacccgg tttgcctgcc atacataaat ctgaagcgat tgctgaactc | 780 |
| tccgctgccg tcggcctgca gggcttagtg caagggcaat tccaggatct gcacgacggc | 840 |
| acgcagagcc gcagcccgga agcgatcgcc atgaccaacg aactgaaaac cagcgtgctg | 900 |
| tttcgcgcca cgctgcaaat ggcggcgatt gccgctgacg cttcaccgca ggtgcggcaa | 960 |
| agacttagct tcttcgccca ggatttgggc caggcgtttc aactgctcga cgacctcgcc | 1020 |
| gacggttgca aacacaccgg taaagatgtg caccaggatc agggcaaatc cacgctggta | 1080 |
| cagatgctcg gtgctgacgg cgcggaacgt cgcctgcgcg atcacctgcg cagcgcagat | 1140 |
| gcacaccttg cctgcgcctg ccatcgcggc atcgccactc gccaatatat gcacgcgctg | 1200 |
| tttaatcaac agctagcgat attcaactga gcgcggctca gccggtgggc cactttgcgg | 1260 |
| tgatcgcgcc gccgctctac agccactttc acgcgttgca ggcgttagca caaacgctgc | 1320 |
| tggcgcgcgg ccatcgcatc acattcatcc agcaagccga tgcccgcact ttgcttagcg | 1380 |
| acgaacgcat cgattttgtt gccgtcggcc aacagacgca tcctgccggt tcgctggcgc | 1440 |
| ccgtgttgca tcggctggcc tcgcggggcg gcctgtcgct gtttcgcgtg atcgacgatc | 1500 |
| tcgcgtcctg caccgatatg ctgtgccgcg aactgcctgc ggtactgaaa gcattgaaca | 1560 |
| tcgatggcgt gatcgccgac gaaatggaag cggcgggcgg attggtcgct gaagcgctgc | 1620 |
| atctgccgtt tgtttcggtg gcctgcgcct tgccggtcaa tcgtgaagcc gggattccgc | 1680 |
| ttgcggtgat gcccttccgt tttgcacagg atgacaaagc gctgaaacgt tttcaggcca | 1740 |
| gcagcgatat ctatgatcgc atcatgcgtc gtcacggcga cgtgatcctc aaacacgcgc | 1800 |
| gggcgtttaa tttgacggag cggcgcggat tacatcagtg cctgtcgccg ctggcacaaa | 1860 |
| tcagccagat ggtgccggcc tttgatttc cacgtcagca actgcccgcc tgctatcacg | 1920 |
| ccgtggggcc actccgcgcc ccggtttctc ctgcgccgct ccatgcgccc tggccagcgc | 1980 |
| tgcgtcagcc ggtggtttat gcctcgctgg gtacgctgca aggccatcgc ttccggctgt | 2040 |
| ttctgcatct ggcgcaggcg tgccgccagc tgcggctatc gctggtgatc gcccattgtg | 2100 |
| ggggattaaa cgccgaacag acgcatcagc tggagctcgc tggcgcggcg tgggtgacgg | 2160 |
| atttcgtcga tcagcgcgca gccctacagc acgcgcagct gtttatcact catgccgggt | 2220 |
| taaacagcgc gctggaagca ctggaatgcg gtacgccgat gctggcgctg ccgattgctt | 2280 |
| ttgatcagcc cggcgtggcg gcgcgcattg agtggcatga cgttggtcgc cgcgcatcac | 2340 |
| gctttagccg tgttcatcaa ctggagcagc atctgcaaca gctgctgacc gacgatcgtt | 2400 |
| acgcgctacg gatgtcagcg attcaggcgc agctgcagcg cgcaggcggt tgccagcgtg | 2460 |
| ccgccgacat cgtcgagcag gcgctgtgcc agcagcaagt cgtgctggcg gaggcgacct | 2520 |
| gatgcgcacg caatacgatg tgattttggt cggtgctgga ctggcgaatg gcttgattgc | 2580 |

-continued

```
gctgcgtctg cgtcaattgc agccacaact gaaatgcctg ttgctggaga gcgatgcgca    2640
tccggcaggc aatcatacct ggtcgtttca tcacagcgat ctcagcgccg aacaacttcg    2700
ctggctgcaa ccgctgatta ccgtgcgttg gtcaggttat caggtgcgtt ttcctgcgct    2760
gcgccgcaat ctggacgggg attattgttc catcgcatca ggcgattttg cccgccatct    2820
ttacgcggcg atgggtgacg atctgtggac aaacacagcc gtacaacagg taaaacccac    2880
gcaggtgacg ctggcggatg ccgtgaact tgctgcgcaa gtggtgattg atggtcgcgg     2940
cctgcagccg acgccacatc tgcagctggg ttatcaggtg tttcttggac aagagtggca    3000
gctggcgcag ccgcacggcc tgcagcagcc gatcctgatg gatgccaccg tcgatcagca    3060
agcgggttat cgttttgtct acacgctgcc gctcagcgcc gatcggctat tgattgaaga    3120
tacccattac gttaaccagc ccgcgctggc ggagaacacc gctcgtcagc acatcgccga    3180
ctatgccaat cagcaaggct ggacgctgag tacgctgctg cgtgaagagc acggcatatt    3240
accgattacc ctgagcggca acatcgatcg attctggcaa cagcagcgcg ccaagcgtg    3300 cagcggcctg cgcgccgggc tgtttcatgc caccaccggt tactccttgc cgtccgccgt    3360
ggcgctagcg gagttggtag cagcgctgtt gcccaccgat gccctcacgc tcagccaaca    3420
tatcgaacgc tttgcccgtc agcagtggcg cgaacagcga ttttccgtc tgctaaaccg     3480 catgctgttt ttggccggta agccgcagca gcgctgcgc gtgatgcaac gttttaccg      3540 gctcgatgcc gggttaatta gccgcttta cgccggcaa ctgcgcctgc gcgataaaac      3600
gcggattctg tgcggcaagc cgccggtgcc catcggtgaa gcgctgcgcg cgctgttgaa    3660
ttctgtcgaa ccagggaaga aaaatgaaa cgcacttatg tgattggcgc aggctttggc     3720
ggcctggcgc tggcgattcg cctgcaagcg gcgggcatac caaccacctt actcgagcag    3780
cgcgacaaac cgggcggacg cgcctatgtg tttgaggaca gtggctttac cttcgatgcc    3840
ggacccacgg tgatcaccga tcccagcgcc atcaagagt tgttcacgct ggcaggaaaa    3900
tcgctcagcg attacgtcga gctgatgccg gtaacgccct ctatcgcct gtgctgggaa    3960 gatggcaaac agcttgatta cgacaataat cagccgctgc tggagcagca gatcgccacg    4020
ttcaatccgc aagatgtaga aggctatcgt caatttcttg cctattcacg tgaagtattt    4080
agagagggtt atctgaaact cggcacggtg ccgtttctgc aggtgcgtga catgctgcgc    4140
gtcgcgccgc agttgggacg tctgcaagca tggcgcagcg tctacagcat ggtggcgaaa    4200
tttattcagg acgatcatct gcgtcaggcg ttttccttcc actcattgct ggtgggcggt    4260
aatccttttg caacgtcatc gatctatacc ttaattcatg cgctggagcg tgaatggggc    4320
gtgtggtttc cgcgcggcgg caccggcgcg ctggtcagg gcatggcgcg actgttcgag    4380
gacttgggcg gcgagctgtt actgaatgcc gaagtgagcc agctggaaac cagcggcaat    4440
cgcattagcg gcgttcagtt agagggcgga cgacgcttcg atgccgccgc tgtggcctcc    4500
aatgccgacg tggtgcatac ctacgacaaa ctgcttcgcc accatccgct ggcaatgaaa    4560
cgtgcgacat cgctgaagcg taagcgcatg agcaactcgc tgtttgtact ctattttggc    4620
ctgaatcagc cgcatgaaca gctcgcgcac cacaccgtct gttttggccc gcgttatcgt    4680
gagttgatcg atgagatttt caacagcagc cagctggcag acgatttttc actttacctg    4740
cacgcgccct gcagcagcga tccgtcgctg gcaccgcccg gctgcggcag cttttatgtg    4800
ttagcgccgg tgccgcatct cggcaccgct gacatcgact ggcaacagga aggaccgcgc    4860
ttgcgcgatc gaattttttgc ttatctggag cagcactaca tgccgggatt acgtcagcaa    4920
```

-continued

```
ttagtgacac acagaatgtt tacgccgttt gattttcgcg acacgctgca tgcccatcac    4980
ggctcggcgt tttcgctgga gccgattttg acgcaaagcg cctggttccg cccgcataac    5040
cgcgatgccg atatcagcaa tctctatctg gtgggtgccg gtacgcatcc aggcgcgggc    5100
gtgcccggcg tgatcggttc ggccaaggcc accgccaggc tgatgctgga ggatcgcgcc    5160
gaatgaatcg acagccttta cttgagcaag taacgcaaac catggcggtg ggctcgaaga    5220
gtttcgccac cgccgccaag ctgtttgatg caccgacgcg ccgcagcacg ctgatgctgt    5280
atgcgtggtg tcgtcactgc gatgatgtga ttgatgggca aacgctgggc gaaggcggca    5340
cgcagcatgc cgtcgaagac gcgcaggcac gtatgcagca tctgcaaatt gaaacccgcc    5400
gcgcctacag cggcgcgcac atggatgaac cggcgtttag ggcgtttcag gaagtggcga    5460
tcattcacca gctgccgcaa caactggcgt ttgatcatct ggaaggcttc gctatggatg    5520
cacgcaacga acattacgcg agcttcgatg acacgctgcg ttactgctat cacgtcgcgg    5580
gcgtggtcgt tttgatgatg gcgcgcgtaa tgggcgtgcg cgacgaagcg gtgctcgatc    5640
acgcctgcga tttaggactg gcgttccagc tcactaacat tgcgcgcgac attgtagaag    5700
atgccgaaaa tggtcgctgc tatctgccgc aatcctggct cgatcaggcg ggattacgcg    5760
ccgatacgct gactgcaccg caacatcgtg cagcgctcgc ctcactggca gcgcgtttag    5820
tggcggaggc ggaaccctat tatcactcgg cgcgatccgg tttaccgggt ttaccgctgc    5880
gctcggcgtg ggccatcgct acggctcgcg gcgtttatcg cgaaattggc gtcaaagttc    5940
agcacgccgg tgtgcacgcc tgggattcac ggcagcgcac cagtaaaggt gaaaaactgg    6000
cgctgctggt gaaaggggca ggtttggcga tcacttcgcg tgtgtctcgt cctgaaccgc    6060
gtccggctgg tctgtggcag cgtcctcgtt gattttacgt ccgtgacgct ggcgcagcgt    6120
ggcttgcagc ttattcagcg gtggcgcgta gaggaaacca aacgacacgc agccttcacg    6180
cccgcgcacc gcatgatgca tgcggtgcgc catgtataag cgcttaagat agcctttgcg    6240
cgggatatag cggaacggcc agcgttgatg caccaggcca tcgtgcacca tgaagtagag    6300
cgcgccgtac gtcgtcattc cggcaccaat ccactgcagc ggccacatgc cttgcacacc    6360
gacataaatc agcacaatcg ccagtaccgc aaacaccacc gcataaagat cgttgagctc    6420
aaacttaccg ctgtgcggtt catggtgcga cagatgccag ccccatcccc aaccgtgcat    6480
gatgtattta tgcgacagcg ccgctacgat ttccatcacc accacggttg ccaacaagat    6540
aagcacgttc cataaccaga gcattgttcg tccatttgtg gaaagggaa gtactaaagg    6600
tggacgcgga tgagtgatgg cgcaaggttt accatgttta gaaattttaa aagtccataa    6660
cacgttatga acgctgcatt gcagaaagcg cagatttcac acatactcac cacacttatc    6720
aatacacgtg ttaactacat ggggatttta tgccttctac agccgtaaga caaaaaaaa    6780
ctgtcagtgt gacacttgaa cctgctctac tcgagcaagc cagagaggca gggctcaatt    6840
tatccgccat cctatccaaa gctttgcaac atgaaattcg cacgactgca gcagaaagat    6900
ggaagcgtga aaacagtgaa ggtttgcagg aactcaatcg cataaccgaa gagcacggtt    6960
tattgtcgga tgaatacagg acgttttaga catgcaata                         6999
```

<210> SEQ ID NO 7
<211> LENGTH: 31
<212> TYPE: DNA
<213> ORGANISM: Artificial sequence
<220> FEATURE:
<223> OTHER INFORMATION: primer

<400> SEQUENCE: 7

```
gaattcacca accatggata gccattatga c                                      31

<210> SEQ ID NO 8
<211> LENGTH: 26
<212> TYPE: DNA
<213> ORGANISM: Artificial sequence
<220> FEATURE:
<223> OTHER INFORMATION: primer

<400> SEQUENCE: 8
gaattcaacg aggacgctgc cacaga                                            26

<210> SEQ ID NO 9
<211> LENGTH: 34
<212> TYPE: DNA
<213> ORGANISM: Artificial sequence
<220> FEATURE:
<223> OTHER INFORMATION: primer

<400> SEQUENCE: 9
gaattcacta gtcgagacgc cgggtaccaa ccat                                   34

<210> SEQ ID NO 10
<211> LENGTH: 25
<212> TYPE: DNA
<213> ORGANISM: Artificial sequence
<220> FEATURE:
<223> OTHER INFORMATION: primer

<400> SEQUENCE: 10
gaattctagc gcgggcgctg ccaga                                             25

<210> SEQ ID NO 11
<211> LENGTH: 5632
<212> TYPE: DNA
<213> ORGANISM: Pantoea agglomerans DC404

<400> SEQUENCE: 11
catgaccggc ggcgcggcgc gcgccagaga cattaaccgt catctggccc aggcggcgca       60
aacccttggg ctggcgatgg gcgtcggttc ccagcgcgtg gcgctggagg acggcgcgca      120
gcacgggctg gatgcccagc tacgccatat cgccccggac gtgccgctgc tggctaacct      180
tggcgcggcg cagatccgcg gtgcgcaggg gctggactac gcccggcgcg cggtggacat      240
gatcgacgcc gacgcgttaa ttgtgcatct gaacccgctg caggaggcgc tccagggcgg      300
cggcgatcgc gactggcgcg gcatcctcaa cgccattgcg cagctggtgc gcgacctgcc      360
ggtaccggtg gtggttaaag aggtgggcgc cgggatctcc ccggacgttg cctgccgact      420
ggcggacgtc ggcgtggcga tgatcgacat gccggcgcg gcggaaccga ctgggcggc       480 ggtggaagct gaacgcgccc cgaccccga ggcgcgaaat gtggcgatgg cctttgccga      540 ctgggcatt cctactgccg atgcgctgcg tcgcgtccat cttgcgctgc tgatatccc       600 gcttatcgcc tccggcggca tcgccaacg cattgacgca gcaaaagcca tcgcgctggg      660
tgcagatctg gtgggccagg ccgcggcggt gctggcgcat gccaacgcct ccggcgacgc      720
ggcaattgcc catttccgca ccctgattac gcagctgcgg atcgcctgtt tctgtaccgg      780
cagtgcaaac ctgcaggcgt tgcgacacgc cacgctgctt ccggtcaacg gcggcgcatc      840
cctgtgacgc agtacggtgc cttataccgg ggagcggtat gaaaaatgg gatctgattc       900 tggtcggcgc ggggctggcc aacgggctta tcgcctggcg actaaagcag cgtcatccga      960
```

```
cgcttgctgt attaatgctg gagtgcggcg acgcgcccgg cggaaaccac acctggtcct   1020
ttcaccaaca cgatatcacg ccagcccagc acgcctggct ggcgccgctg gtggcccatc   1080
gctgggacgg gtacgacgtc cactttccga acgtgtcgcg caccctgcat gacggctacc   1140
tgaccatcac ctccacgcgt tttgcccaag cgatgcgcgg gctgatgaaa gagaatttgc   1200
tgacaaacgt gaccgtgtca cgggtgagcg gcaggaagt aaccctcagc gacggacgac   1260
gctttaccgc cggggcggtg attgatggcc gcggctatca gccctcgccg cacctcagca   1320
ttggctatca ggcgttcatc ggccaggagt ggcaactgac cgcgcccac gggttaacgc   1380 gcccgatcct gatggatgcc cgcgtcgccc agggcaacgg ctaccgcttt gtctatacccc   1440 tgccgctcag cgccgacacc ctgcttatcg aagacacgca ctacattgac ggcccgacgc   1500
tcgacgccga ttcagcccgc gcgcggattg ccgattacgc ccgccagcag ggctggcagc   1560
ttgcgcggct ggtgcgtgag aacagggggg cgctgccgat caccctgtcc ggcgatccgg   1620
ccgccttctg gcaccagttc catcatcagc cggtcagcgg cctgcgcgcc ggtctgttcc   1680
atgccaccac cggctattcg ctgccgctgg cggttcggct ggcggaccgc attgccaacg   1740
cgccgggact gcatcagggc gcgctctatc agctgatcgc cgatttcgcg gcgcgccact   1800
ggcagacaca acgcttttc cgcctgctta accgcatgct tttcctggcc ggcacacccg   1860
accagcgctg gcgcgtgatg cagcggtttt accagcttga cgagcagctg atcgcccgtt   1920
tttatgccgg ccagcttcgc tccgccgacc gcgcgcgcct gctgcttggc aaaccgccgg   1980
tgccgattgt cggggcgatc aaagccctgc tccacactca ttcttctctg cgagcccatc   2040
ataaatgaaa caaaccattg taattggcgc cgggttcggc ggactggcgc tggcgattcg   2100
cctccaggcg gcgggcattc ctaccacgct gctggagagc cgcgacaaac ccggcggccg   2160
cgcctatgtc tacgaagatc gcggctttac ctttgatgcg ggtcccaccg tcatcaccga   2220
tccctccgcc attgaggagc tgttcacccct gccggaaaaa cggctgaagg actacgttga   2280
gctgatgccg gtgacgccgt tctatcgcct gtgctgggaa gacggcaagg ttttcgacta   2340
cgccaacgat caggcggcgc ttgagtcgca gatcgccgcg tttaacccga cgacgtggc   2400 gggctatcac cgcttcctcg actactcccg ggcggtgttt gccgaaggct atctgaagct   2460
cggcgcggtg ccgttctctct cgtttcgcga catgctgcgc gccggtcctc aactggcgcg   2520
gctgcaggca tggcgcagcg tgtacgacaa agtgtcggcc tacgtggaag acgagcacct   2580
gcggcaggca ttttcgttc actcgctgct ggtgggcggc aacccgttct ccacgtcttc   2640
tatttacacc ctgatccacg ccctggagcg ggaatggggc gtctggttcc cgcgcggcgg   2700
caccggtgcg ctggttcagg gcatggtgaa gctgtttcag gatcttggcg gcaccctcac   2760
ccttaacgct caggttgagc ggctggagac ggtggacaat caggtgaagg ccgtgcatct   2820
ggttaacggg cagcggctgg aggctgcggc ggtggcctcg aacgcggacg tggtaaatac   2880
ctatgcccga ctgctcggcc atcacccgca cggcgccgct acggcaaaaa agctgaaacg   2940
caagcgcatg agcaactcgc tgttcgtgct ctatttggc ctggatcacc atcacaccca   3000
gctggcgcac cataccgtct gctttggccc gcgttataaa gcgctaatcg atgaaatttt   3060
cagcgccgac accctgtcgg aagatttttc gctctatctg catgcgccct gcgtaaccga   3120
cccgtcgctg gccccgccgg ggtgcggcag ctactatgtg ctcgcgccgg tgccgcacct   3180
cggtaacgcc ccgctcgact ggagcgtgga agggccgcgt ctgcgggatc gcatttttga   3240
ttatctcgaa gcgcgctata tgccggggct gcgctcccag ctggtgacgc accgcatgtt   3300
cacgccggaa gattttcgcg atacgctcga tgcctggcag gggtcagcgt tttcactgga   3360
```

-continued

```
gccgatcctc acccagagcg cctggttccg gccgcacaac cgcgacagcg tggttgataa    3420
cctctacctg gtcggcgccg aacgcatcc cggcgctggc gtgccgggcg tgatcggatc     3480
cgccaaggca acgcccagt taatgttaaa ggatttagcg taatgtccca gccgcttctc     3540
gaacacgcca gcgccaccat gaccgccggt tctaaaagtt tcgccaccgc ctcaaagctg    3600
tttgacaaac gcaccggcg cagcgcgctg atgctctata cctggtgccg ctactgcgac     3660
gatgttatcg acggacaggt ggtgggtttt gctgccccga ccgagcagag cgacacgccc    3720
gaggcgcgcc tgcaacggct gcgtaagatg acgcgccgcg cctacgacgg ggaaaccatg    3780
caagagccgc cgttcgccgc ctttcaggag gttgccctcg cccatgccat tccgcctact    3840
caggccttcg accacctgga aggctatgcg atggacgtgc gcaacgagcg ctattacagc    3900
ctcgatgata cgctccgcta ctgttatcac gtggcgggcg tggtcggcct gatgatggcc    3960
agggtgatgg gagtgcggga cgaagccacg ctggatcgcg cctgcgatct gggcattgcc    4020
tttcagctca ccaatatcgc cagggatatc gttgacgatg cgcaggtggg acgctgctac    4080
ctgccgcagc agtggctggc ggaagtcgga ctcaatgaac agacctgcac cgtgcgggcc    4140
aaccgtccgg cgctggcgcg tctggcagcg cggctggtga ccgaggctga gccctattat    4200
cagtcagcgc ttgccgggct gggggatctg ccccctgcgct ccgcctgggc gattgccacc    4260
gcgcacgggg tgtatcgtga gatcgggtg aaggtgctga tggcgggtga aaaagcatgg     4320
gatacccgcc agggcacgac gcgcgcggag aagctggcgc tggttatttc cggcgcgaag    4380
caggcgatgg cttcccggaa ggcgagctgg ccgccgcgcg atccgcacct ctggcagcgc    4440
ccgcgctaga attcgaattc actagtcgag acgccgggta ccaaccatga caagacccttt   4500 tgaaacacat cccggtcacg acggggaact gcatgagctg cacgctgccc tgcaacgtcg    4560
cctggatgaa ctgctgcccg ttggcgatga gcgggatcgg gtcagcagcg caatgcgcga    4620
aggcgtactg gcaccgggga aacgcattcg cccgctgctc ctgatcctcg ccgcccgcga    4680
cctcggctgc gatcgcgacc accccggcct gctggatatg gcctgtgcgg tggaaatggt    4740
gcacgcctcg tcgctgatcc tcgacgatat tccctgcatg gataacgcgg cgctccggcg    4800
cggtcgccct accattcatc gccagtatgg tgaagacgtg gcaattctcg ctgcggtagc    4860
gttgctcagc agcgcctttg gcgtgatggt cgcggcgcag ggattgtctc ccgagtgccg    4920
cagccaggcg gtggcggagc tgtcgatggc ggtcggtacc cagggtctgg tgcagggtca    4980
gtataaggat ctgcgtgaag gcaccgcccc gcgcagcgcc gaggagatcg ccaccaccaa    5040
cgaactgaaa accagcgtgc tgtttggtgc cacgctgcaa atcgcggccc tggcggcagg    5100
cgcctcgccg gcgcgcgcc agaaaatgcg ctgctttgcg caggatttag gccaggcgtt    5160
ccagctgctg gacgatctgg cggacggcca tgccgggacc ggcaaagaca tcaataagga    5220
cgcgggtaag tccacgctgg tggcgatgct cggcagcgac gcggtgcgcg agcggctcga    5280
cacccatctg cgccgcgcag acgcccattt ttcacgcgcc tgcggaaaaa accaggccac    5340
gcgacgcttt atgcacgcct ggttttcaaa acagctggcc gcgtttagct gagcaacgga    5400
tacaccccgg taatatttgt ggagatcaca tgaaggacgc gcatctggtt cagcgtaaaa    5460
atgaccacct ggatatcgtg ctgcaccctg accgggcgat gagtaccatt cgcaccggat    5520
ttgacgcctg gcgttttgaa cactgcgccc tcccggagct ggatctcgac ggtatcgatc    5580
tctccaccac cctgtttttcc cgcccgctga agccccggt gctgatcagc tc            5632
```

<210> SEQ ID NO 12

<211> LENGTH: 780
<212> TYPE: DNA
<213> ORGANISM: Brevunidmonas vesicularis DC263

<400> SEQUENCE: 12

| | | | | | |
|---|---|---|---|---|---|
| atgcggcaag | cgaacaggat | gcttaccggg | ccgcgatgcg | ctaagtgtcg | cgccatgtcc | 60 |
| gccgtcacgc | caatgtcacg | ggtcgtcccg | aaccaggccc | tgatcggcct | gacgctggct | 120 |
| ggcctgatcg | ccgcggcctg | gctgaccctg | cacatctacg | gcgtctattt | tcatcgctgg | 180 |
| acgatctgga | gcgtcctgac | cgttccgctg | atcgtcgccg | ccagacctg | gctatccgtc | 240 |
| ggcctgttca | tcgtcgccca | cgacgccatg | cacggctcgc | tggccccggc | acgcccacgg | 300 |
| ctgaacacgg | cgatcggcag | cctggcgctg | gccctctacg | ccggatttcg | gttcacgcct | 360 |
| ttgaagaccc | acaccacgc | ccatcacgct | gcgcccggta | cggcggacga | tcccgacttt | 420 |
| cacgccgacg | ccccgcgcgc | tttcctgccc | tggttctacg | gcttttttccg | cacctatttc | 480 |
| ggctggcgag | aactgccgt | tctgacggtg | ctcgtggccg | ttgcggtgct | gatcctcggc | 540 |
| gcccgtatgc | ccaatcttct | ggtcttttgg | gccgcgcccg | ccctgctctc | ggcgctacag | 600 |
| cttttcacat | tcggcacctg | gctgcctcat | aggcacaccg | acgacgcctt | ccccgacaac | 660 |
| cacaacgccc | gcaccagccc | cttcggcccg | gtcctgtcgt | tgctcacctg | cttccacttc | 720 |
| ggccgccacc | acgaacacca | cctgacccc | tggaagccct | ggtggagttt | gttcagctag | 780 |

<210> SEQ ID NO 13
<211> LENGTH: 747
<212> TYPE: DNA
<213> ORGANISM: Sphingomonas melonis DC18

<400> SEQUENCE: 13

| | | | | | |
|---|---|---|---|---|---|
| atgaccgtcg | atcacgacgc | acggatcagc | ctgctgctgg | ccgcagccat | cggcgccgcg | 60 |
| tggctggcga | tccatgtcgg | ggcgatcgtg | tggtggcgat | ggagcccggc | gacggcggtg | 120 |
| ctcgcgatcc | ccgtcgtgct | cgtacaggcg | tggctgagca | ccggcctgtt | catcgtcgcg | 180 |
| cacgattgca | tgcacggatc | gttcgtgccc | ggccggcccg | cggtcaaccg | gaccgtcggg | 240 |
| acgctgtgcc | tcggcgccta | tgcgggactg | tcctatggcc | agctccatcc | caagcatcat | 300 |
| gcgcatcacg | atgcgccggg | caccgccgcc | gaccccgatt | ccatgccgg | cgcgccgcga | 360 |
| tccgcactgc | cgtggttcgc | gcgcttcttc | accagctatt | acacgcacgg | ccagatcctc | 420 |
| cggatcaccg | cggcggcggt | gctgtacatg | ctgctcggtg | tgtcgctgct | caacatcgtc | 480 |
| gtgttctggg | cgttgccggc | gctgatcgcg | ctggcgcagc | tgttcgtctt | cggcaccttc | 540 |
| ctgccgcatc | gccacggcga | cacgccgttc | gcggacgcgc | acaatgcccg | cagcaacggc | 600 |
| tggccacggc | tggcgtcgct | ggcgacctgc | ttccacttcg | gcgcctatca | tcacgaacat | 660 |
| cacctgagcc | cgtggacgcc | ctggtggcag | ttgccgcgcg | tcggccagcc | tgccgccgga | 720 |
| caccggtcgt | taagcaaaga | ccggtag | | | | 747 |

<210> SEQ ID NO 14
<211> LENGTH: 22
<212> TYPE: DNA
<213> ORGANISM: Artificial sequence
<220> FEATURE:
<223> OTHER INFORMATION: primer

<400> SEQUENCE: 14
gttcgaactg gggaaaacgg ac                                              22

<210> SEQ ID NO 15
<211> LENGTH: 22
<212> TYPE: DNA
<213> ORGANISM: Artificial sequence
<220> FEATURE:
<223> OTHER INFORMATION: primer

<400> SEQUENCE: 15
caaaggcgtg aaccgaaatc cg           22

<210> SEQ ID NO 16
<211> LENGTH: 486
<212> TYPE: DNA
<213> ORGANISM: Brevundimonas vesicularis DC263
<220> FEATURE:
<221> NAME/KEY: CDS
<222> LOCATION: (1)..(486)

<400> SEQUENCE: 16

| atg | tcc | tgg | ccg | acg | atg | atc | ctg | ctg | ttc | ctc | gcc | acc | ttc | ctg | ggg | 48 |
| Met | Ser | Trp | Pro | Thr | Met | Ile | Leu | Leu | Phe | Leu | Ala | Thr | Phe | Leu | Gly | |
| 1 | | | | 5 | | | | | 10 | | | | | 15 | | |

| atg | gag | gtc | ttc | gcc | tgg | gcg | atg | cat | cgc | tat | gtc | atg | cac | ggc | ctg | 96 |
| Met | Glu | Val | Phe | Ala | Trp | Ala | Met | His | Arg | Tyr | Val | Met | His | Gly | Leu | |
| | | | | 20 | | | | | 25 | | | | | 30 | | |

| ctg | tgg | acc | tgg | cac | cgc | agc | cat | cat | gag | ccg | cac | gac | gac | gtg | ctg | 144 |
| Leu | Trp | Thr | Trp | His | Arg | Ser | His | His | Glu | Pro | His | Asp | Asp | Val | Leu | |
| | | 35 | | | | | 40 | | | | | 45 | | | | |

| gaa | agg | aac | gac | ctg | ttc | gcg | gtg | gtg | ttc | gcc | gcc | ccg | gcc | atc | atc | 192 |
| Glu | Arg | Asn | Asp | Leu | Phe | Ala | Val | Val | Phe | Ala | Ala | Pro | Ala | Ile | Ile | |
| 50 | | | | | 55 | | | | | 60 | | | | | | |

| ctc | gtc | gcc | ttg | ggt | cta | cat | ctg | tgg | cct | tgg | atg | ctg | ccg | atc | ggc | 240 |
| Leu | Val | Ala | Leu | Gly | Leu | His | Leu | Trp | Pro | Trp | Met | Leu | Pro | Ile | Gly | |
| 65 | | | | | 70 | | | | | 75 | | | | | 80 | |

| ctg | ggc | gtt | acg | gcc | tat | gga | ctg | gtt | tat | ttc | ttc | ttt | cac | gac | ggg | 288 |
| Leu | Gly | Val | Thr | Ala | Tyr | Gly | Leu | Val | Tyr | Phe | Phe | Phe | His | Asp | Gly | |
| | | | | 85 | | | | | 90 | | | | | 95 | | |

| ctg | gtg | cat | cgc | cgg | ttc | ccg | aca | ggg | atc | gca | ggg | cgc | tcg | gcg | ttc | 336 |
| Leu | Val | His | Arg | Arg | Phe | Pro | Thr | Gly | Ile | Ala | Gly | Arg | Ser | Ala | Phe | |
| | | 100 | | | | | 105 | | | | | 110 | | | | |

| tgg | acg | cga | cgc | att | cag | gcc | cac | cgg | ctg | cat | cac | gcg | gtg | cgg | aca | 384 |
| Trp | Thr | Arg | Arg | Ile | Gln | Ala | His | Arg | Leu | His | His | Ala | Val | Arg | Thr | |
| | | | 115 | | | | | 120 | | | | | 125 | | | |

| cgc | gag | ggc | tgc | gta | tcg | ttc | ggc | ttc | ctt | tgg | gtg | cgg | tcg | gcg | cgc | 432 |
| Arg | Glu | Gly | Cys | Val | Ser | Phe | Gly | Phe | Leu | Trp | Val | Arg | Ser | Ala | Arg | |
| | 130 | | | | | 135 | | | | | 140 | | | | | |

| gcg | ctg | aag | gcc | gaa | ctg | tct | cag | aaa | cgc | ggc | tca | tcc | agc | aac | ggc | 480 |
| Ala | Leu | Lys | Ala | Glu | Leu | Ser | Gln | Lys | Arg | Gly | Ser | Ser | Ser | Asn | Gly | |
| 145 | | | | | 150 | | | | | 155 | | | | | 160 | |

| gcc | tga | | | | | | | | | | | | | | | 486 |
| Ala | | | | | | | | | | | | | | | | |

<210> SEQ ID NO 17
<211> LENGTH: 161
<212> TYPE: PRT
<213> ORGANISM: Brevundimonas vesicularis DC263

<400> SEQUENCE: 17

| Met | Ser | Trp | Pro | Thr | Met | Ile | Leu | Leu | Phe | Leu | Ala | Thr | Phe | Leu | Gly |
| 1 | | | | 5 | | | | | 10 | | | | | 15 | |

| Met | Glu | Val | Phe | Ala | Trp | Ala | Met | His | Arg | Tyr | Val | Met | His | Gly | Leu |
| | | | | 20 | | | | | 25 | | | | | 30 | |

```
Leu Trp Thr Trp His Arg Ser His Glu Pro His Asp Asp Val Leu
        35                  40                  45

Glu Arg Asn Asp Leu Phe Ala Val Val Phe Ala Ala Pro Ala Ile Ile
 50                  55                  60

Leu Val Ala Leu Gly Leu His Leu Trp Pro Trp Met Leu Pro Ile Gly
 65                  70                  75                  80

Leu Gly Val Thr Ala Tyr Gly Leu Val Tyr Phe Phe Phe His Asp Gly
                 85                  90                  95

Leu Val His Arg Arg Phe Pro Thr Gly Ile Ala Gly Arg Ser Ala Phe
                 100                 105                 110

Trp Thr Arg Arg Ile Gln Ala His Arg Leu His His Ala Val Arg Thr
             115                 120                 125

Arg Glu Gly Cys Val Ser Phe Gly Phe Leu Trp Val Arg Ser Ala Arg
 130                 135                 140

Ala Leu Lys Ala Glu Leu Ser Gln Lys Arg Gly Ser Ser Ser Asn Gly
 145                 150                 155                 160

Ala

<210> SEQ ID NO 18
<211> LENGTH: 489
<212> TYPE: DNA
<213> ORGANISM: Agrobacterium aurantiacum

<400> SEQUENCE: 18
atgaccaatt tcctgatcgt cgtcgccacc gtgctggtga tggagttgac ggcctattcc      60
gtccaccgct ggatcatgca cggcccctg  ggctggggct ggcacaagtc ccaccacgag     120
gaacacgacc acgcgctgga aaagaacgac ctgtacggcc tggtctttgc ggtgatcgcc     180
acggtgctgt tcacggtggg ctggatctgg gcgccggtcc tgtggtggat cgccttgggc     240
atgactgtct atgggctgat ctatttcgtc ctgcatgacg gctggtgca tcagcgctgg      300 ccgttccgtt atatcccgcg caagggctat gccagacgcc tgtatcaggc ccaccgcctg     360
caccatgcgg tcgaggggcg cgaccattgc gtcagcttcg gcttcatcta tgcgccccg     420 gtcgacaagc tgaagcagga cctgaagatg tcgggcgtgc tgcgggccga ggcgcaggag     480
cgcacgtga                                                              489

<210> SEQ ID NO 19
<211> LENGTH: 519
<212> TYPE: DNA
<213> ORGANISM: Novosphingobium aromaticivorans ATCC 700278
<220> FEATURE:
<221> NAME/KEY: CDS
<222> LOCATION: (1)..(519)

<400> SEQUENCE: 19 atg cag acg ctt gcc gcg atc ctc att gtc ctg ggc acg gtc ctc gcg        48
Met Gln Thr Leu Ala Ala Ile Leu Ile Val Leu Gly Thr Val Leu Ala
 1               5                  10                  15 atg gaa ttc gtc gcg tgg tcg agc cac aag tac atc atg cac ggc ttc        96
Met Glu Phe Val Ala Trp Ser Ser His Lys Tyr Ile Met His Gly Phe
                 20                  25                  30 ggc tgg ggc tgg cac cgc gac cat cat gag ccg cac gaa ggg ttt ctc       144
Gly Trp Gly Trp His Arg Asp His His Glu Pro His Glu Gly Phe Leu
             35                  40                  45 gag aag aac gat ctc tac gcc att gtc ggc gcg gcg ctt tcg atc ctg       192
Glu Lys Asn Asp Leu Tyr Ala Ile Val Gly Ala Ala Leu Ser Ile Leu
 50                  55                  60
```

```
atg ttc gcg ctg ggc agc ccg atg atc atg ggc gcg gat gcc tgg tgg      240
Met Phe Ala Leu Gly Ser Pro Met Ile Met Gly Ala Asp Ala Trp Trp
 65                  70                  75                  80 ccg ggc acg tgg atc ggc ctg ggc gtc ctg ttc tat ggc gtg atc tat      288
Pro Gly Thr Trp Ile Gly Leu Gly Val Leu Phe Tyr Gly Val Ile Tyr
                 85                  90                  95 acg ctg gtg cat gac ggg ctg gtc cac cag cgc tgg ttc cga tgg gtc      336
Thr Leu Val His Asp Gly Leu Val His Gln Arg Trp Phe Arg Trp Val
             100                 105                 110 ccg aag cgc ggc tat gcc aag cgg ctg gtc cag gcg cac aag ctt cac      384
Pro Lys Arg Gly Tyr Ala Lys Arg Leu Val Gln Ala His Lys Leu His
         115                 120                 125 cac gcc acg atc ggc aag gaa ggc ggc gtc agt ttc ggc ttc gtc ttc      432
His Ala Thr Ile Gly Lys Glu Gly Gly Val Ser Phe Gly Phe Val Phe
     130                 135                 140 gcg cgc gac cct gcg gtg ctg aag cag gaa ctg cgg gcc cag cgc gag      480
Ala Arg Asp Pro Ala Val Leu Lys Gln Glu Leu Arg Ala Gln Arg Glu
145                 150                 155                 160 gca ggc atc gcc gtt ctg cgc gag gca gtg gac ggc tag                  519
Ala Gly Ile Ala Val Leu Arg Glu Ala Val Asp Gly
                165                 170
```

<210> SEQ ID NO 20
<211> LENGTH: 172
<212> TYPE: PRT
<213> ORGANISM: Novosphingobium aromaticivorans ATCC 700278

<400> SEQUENCE: 20

```
Met Gln Thr Leu Ala Ala Ile Leu Ile Val Leu Gly Thr Val Leu Ala
  1               5                  10                  15

Met Glu Phe Val Ala Trp Ser Ser His Lys Tyr Ile Met His Gly Phe
                 20                  25                  30

Gly Trp Gly Trp His Arg Asp His Glu Pro His Glu Gly Phe Leu
             35                  40                  45

Glu Lys Asn Asp Leu Tyr Ala Ile Val Gly Ala Ala Leu Ser Ile Leu
         50                  55                  60

Met Phe Ala Leu Gly Ser Pro Met Ile Met Gly Ala Asp Ala Trp Trp
 65                  70                  75                  80

Pro Gly Thr Trp Ile Gly Leu Gly Val Leu Phe Tyr Gly Val Ile Tyr
                 85                  90                  95

Thr Leu Val His Asp Gly Leu Val His Gln Arg Trp Phe Arg Trp Val
             100                 105                 110

Pro Lys Arg Gly Tyr Ala Lys Arg Leu Val Gln Ala His Lys Leu His
         115                 120                 125

His Ala Thr Ile Gly Lys Glu Gly Gly Val Ser Phe Gly Phe Val Phe
     130                 135                 140

Ala Arg Asp Pro Ala Val Leu Lys Gln Glu Leu Arg Ala Gln Arg Glu
145                 150                 155                 160

Ala Gly Ile Ala Val Leu Arg Glu Ala Val Asp Gly
                165                 170
```

<210> SEQ ID NO 21
<211> LENGTH: 42
<212> TYPE: DNA
<213> ORGANISM: Artificial sequence
<220> FEATURE:
<223> OTHER INFORMATION: primer

<400> SEQUENCE: 21
actagtaagg aggaataaac catgtcctgg ccgacgatga tc          42

<210> SEQ ID NO 22
<211> LENGTH: 25
<212> TYPE: DNA
<213> ORGANISM: Artificial sequence
<220> FEATURE:
<223> OTHER INFORMATION: primer

<400> SEQUENCE: 22
tagatcaggc gccgttgctg gatga          25

<210> SEQ ID NO 23
<211> LENGTH: 46
<212> TYPE: DNA
<213> ORGANISM: Artificial sequence
<220> FEATURE:
<223> OTHER INFORMATION: primer

<400> SEQUENCE: 23
actagttcta gataaggagg aataaaccat gcagacgctt gccgcg          46

<210> SEQ ID NO 24
<211> LENGTH: 30
<212> TYPE: DNA
<213> ORGANISM: Artificial sequence
<220> FEATURE:
<223> OTHER INFORMATION: primer

<400> SEQUENCE: 24
gctagcccta ggttagccgt ccactgcctc          30

<210> SEQ ID NO 25
<211> LENGTH: 35
<212> TYPE: DNA
<213> ORGANISM: Artificial sequence
<220> FEATURE:
<223> OTHER INFORMATION: primer

<400> SEQUENCE: 25
gaattcacta gtaccaacca tggatagcca ttatg          35

<210> SEQ ID NO 26
<211> LENGTH: 51
<212> TYPE: DNA
<213> ORGANISM: Artificial sequence
<220> FEATURE:
<223> OTHER INFORMATION: primer

<400> SEQUENCE: 26
atcaggtcgc ctccgccagc acgactttca gttgaatatc gctagctgtt g          51

<210> SEQ ID NO 27
<211> LENGTH: 51
<212> TYPE: DNA
<213> ORGANISM: Artificial sequence
<220> FEATURE:
<223> OTHER INFORMATION: primer

<400> SEQUENCE: 27
caacagctag cgatattcaa ctgaaagtcg tgctggcgga ggcgacctga t          51

<210> SEQ ID NO 28
<211> LENGTH: 49
<212> TYPE: DNA
<213> ORGANISM: Artificial sequence -continued
<220> FEATURE:
<223> OTHER INFORMATION: primer

<400> SEQUENCE: 28
cattttttct tccctggttc gacagagttc aacagcgcgc gcagcgctt           49

<210> SEQ ID NO 29
<211> LENGTH: 49
<212> TYPE: DNA
<213> ORGANISM: Artificial sequence
<220> FEATURE:
<223> OTHER INFORMATION: primer

<400> SEQUENCE: 29
aagcgctgcg cgcgctgttg aactctgtcg aaccagggaa gaaaaaatg           49

<210> SEQ ID NO 30
<211> LENGTH: 26
<212> TYPE: DNA
<213> ORGANISM: Artificial sequence
<220> FEATURE:
<223> OTHER INFORMATION: primer

<400> SEQUENCE: 30
gaattcaacg aggacgctgc cacaga                                    26

<210> SEQ ID NO 31
<211> LENGTH: 42
<212> TYPE: DNA
<213> ORGANISM: Artificial sequence
<220> FEATURE:
<223> OTHER INFORMATION: primer

<400> SEQUENCE: 31
actagtaagg aggaataaac catgcggcaa gcgaacagga tg                  42

<210> SEQ ID NO 32
<211> LENGTH: 28
<212> TYPE: DNA
<213> ORGANISM: Artificial sequence
<220> FEATURE:
<223> OTHER INFORMATION: primer

<400> SEQUENCE: 32
tctagactag ctgaacaaac tccaccag                                  28

<210> SEQ ID NO 33
<211> LENGTH: 42
<212> TYPE: DNA
<213> ORGANISM: Artificial sequence
<220> FEATURE:
<223> OTHER INFORMATION: primer

<400> SEQUENCE: 33
tctagaaagg aggaataaac catgtcctgg ccgacgatga tc                  42

<210> SEQ ID NO 34
<211> LENGTH: 26
<212> TYPE: DNA
<213> ORGANISM: Artificial sequence
<220> FEATURE:
<223> OTHER INFORMATION: primer

<400> SEQUENCE: 34
actagtcagg cgccgttgct ggatga                                    26

```
<210> SEQ ID NO 35
<211> LENGTH: 29
<212> TYPE: DNA
<213> ORGANISM: Artificial sequence
<220> FEATURE:
<223> OTHER INFORMATION: primer

<400> SEQUENCE: 35
ccatgggcta gctaaggatt ggggtgcgt                              29

<210> SEQ ID NO 36
<211> LENGTH: 30
<212> TYPE: DNA
<213> ORGANISM: Artificial sequence
<220> FEATURE:
<223> OTHER INFORMATION: primer

<400> SEQUENCE: 36
ccatggacta gtgtgatgtg ctccgaaagt                             30

<210> SEQ ID NO 37
<211> LENGTH: 31
<212> TYPE: DNA
<213> ORGANISM: artificial sequence
<220> FEATURE:
<223> OTHER INFORMATION: primer

<400> SEQUENCE: 37
actagtaagg aggaataaac catgaccgtc g                           31

<210> SEQ ID NO 38
<211> LENGTH: 31
<212> TYPE: DNA
<213> ORGANISM: artificial sequence
<220> FEATURE:
<223> OTHER INFORMATION: primer

<400> SEQUENCE: 38
atctagatta ccggtctttg cttaacgacc g                           31
```

CAROTENOID HYDROXYLASE ENZYMES

This application claims the benefit of U.S. Provisional Application No. 60/601,947, filed Aug. 16, 2004.

FIELD OF THE INVENTION

This invention is in the field of molecular biology and microbiology. More specifically, this invention pertains to nucleic acid molecules encoding enzymes useful for microbial production of cyclic hydroxylated carotenoid compounds.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in our diet and they play additional important role in human health. Because animals are unable to synthesize carotenoid de novo, they must obtain them by dietary means. Thus, manipulation of carotenoid production and composition in plants or bacteria can provide new or improved source for carotenoids. Industrial uses of carotenoids include pharmaceuticals, food supplements, animal feed additives, and colorants in cosmetics, to mention a few.

Industrially, only a few carotenoids are used for food colors, animal feeds, pharmaceuticals, and cosmetics, despite the existence of more than 600 different carotenoids identified in nature. This is largely due to difficulties in production. Presently, most of the carotenoids used for industrial purposes are produced by chemical synthesis; however, these compounds are very difficult to make chemically (Nelis and Leenheer, *Appl. Bacteriol.* 70:181–191 (1991)). Natural carotenoids can either be obtained by extraction of plant material or by microbial synthesis. However, only a few plants are widely used for commercial carotenoid production and the productivity of carotenoid synthesis in these plants is relatively low. As a result, carotenoids produced from these plants are very expensive.

One way to increase the productive capacity of carotenoid biosynthesis is to apply recombinant DNA technology (reviewed in Misawa and Shimada, *J. Biotech.*, 59:169–181 (1998)). It is desirable to produce carotenoids in non-carotenogenic bacteria and yeasts, thereby permitting control over quality, quantity and selection of the most suitable and efficient producer organisms. The latter is especially important for commercial production economics (and therefore availability) to consumers.

CrtZ-type carotenoid hydroxylases are a class of enzymes that introduce hydroxyl groups to the β-ionone ring of the cyclic carotenoids, such as β-carotene or canthaxanthin, to produce hydroxylated carotenoids. Examples of such carotenoids include astaxanthin, β-cryptoxanthin, zeaxanthin, 3-hydroxyechinenone, 3'-hydroxyechinenone, adonirubin, adonixanthin, tetrahydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal, and lutein.

Carotenoid hydroxylase genes have been reported from a variety of bacterial, fungal, algal, and plant species. Examples of several species include, but are not limited to *Pantoea stewartii* (WO 03/016503; WO 02/079395), *Erwinia uredovora* (EP 393690 B1; Misawa et al., *J. Bacteriol.*, 172(12):6704–6712 (1990)), *Erwinia herbicola* (Hundle et al., *Mol. Gen Genet.*, 245(4):406–416 (1994); Hundle et al., *FEBS Lett.*, 315(3):329–334 (1993); Schnurr et al., *FEMS Microbiol. Lett.*, 78(2–3):157–161 (1991); and U.S. Pat. No. 5,684,238), *Agrobacterium aurantiacum* (Misawa et al., *J Bacteriol.*, 177(22):6575–6584 (1995); U.S. Pat. No. 5,811,273), *Alcaligenes* sp. (U.S. Pat. No. 5,811,273), *Flavobacterium* sp. (U.S. Pat. No. 6,677,134; U.S. Pat. No. 6,291,204; U.S. 2002147371; WO 2004029275; and Pasamontes et al., *Gene*, 185(1):35–41 (1997)), *Paracoccus* sp. (CN 1380415), *Haematococcus pluvialis* (WO 00/061764; Linden, H., *Biochimica et Biophysica Acta*, 1446(3):203–212 (1999)), and plant species such as *Arabidopsis thaliana* (Tian, L. and DellaPenna, D., *Plant Mol. Biol.*, 47(3):379–388 (2001); U.S. 2002102631). Many of these β-carotene hydroxylase genes have been recombinantly expressed in microbial host cells. However, there is a need to identify additional novel crtZ hydroxylase genes useful for genetically engineering commercially-suitable microorganisms for the production of hydroxylated carotenoids, such as astaxanthin and zeaxanthin.

Additionally, there is a particularly important need to identify CrtZ hydroxylases having relatively low to moderate nucleic acid sequence identity (i.e. <70% nucleotide sequence identity) for stable expression of multiple hydroxylase genes as highly homologous genes would be difficult to integrate and tend to result in genetic instability (i.e. undesirable homologous recombination). CrtZ genes having a divergent nucleotide sequences (relative to one another) are most suitable for expressing multiple hydroxylases in a single recombinant host cell. This is especially important when hydroxylase activity becomes the rate-limiting step in the carotenoid biosynthesis pathway. Increasing the number of crtZ genes that can be simultaneously expressed in the production host is expected to increase carotenoid production, assuming that the pool of available substrates is not limiting. This is particularly important when optimizing recombinant production of the desired product (i.e. carotenoids).

The problem to be solved therefore is to provide novel crtZ hydroxylase genes useful for engineering production of carotenoids (i.e. zeaxanthin and astaxanthin).

SUMMARY OF THE INVENTION

The present invention has solved the stated problem by providing a novel crtZ gene, isolated from *Brevundimonas vesicularis* DC263, which is useful for the production of carotenoids in recombinant host cells. Additionally, it has been discovered that a gene from *Novosphingobium aromaticivorans*, previously identified as encoding a hypothetical protein with unknown function, encodes a carotenoid hydroxylase. A method for producing hydroxylated carotenoids using the present CrtZ hydroxylases is also provided.

Accordingly the invention provides an isolated nucleic acid molecule encoding a carotenoid hydroxylase enzyme, selected from the group consisting of:

(a) an isolated nucleic acid molecule encoding an amino acid as set forth in SEQ ID NO: 17;

(b) an isolated nucleic acid molecule comprising a first nucleotide sequence encoding a carotenoid hydroxylase enzyme having at least 95% identity to a polypeptide comprised of an amino acid sequence as represented by SEQ ID NO: 17;

(c) an isolated nucleic acid molecule that hybridizes with
(a) under the following hybridization conditions: 0.1×
SSC, 0.1% SDS, 65° C. and washed with 2×SSC, 0.1%
SDS followed by 0.1×SSC, 0.1% SDS; and (d) an isolated nucleic acid molecule that is complementary to (a), (b), or (c).

Additionally, polypeptides encoded by the present nucleic acid molecules are provided by the invention as well as genetic chimera and transformed hosts comprising the same.

In one embodiment, the invention provides a method of obtaining a nucleic acid molecule encoding a carotenoid hydroxylase enzyme comprising:

(a) synthesizing an at least one oligonucleotide primer corresponding to a portion of the sequence as represented by SEQ ID NO: 16; and (b) amplifying an insert present in a cloning vector using the oligonucleotide primer of step (a);

wherein the amplified insert encodes a carotenoid hydroxylase enzyme.

In another embodiment, the invention provides a method for the production of a hydroxylated carotenoid compound comprising:

(a) providing a host cell which produces cyclic carotenoid having at least one β-ionone ring;

(b) transforming the host cell of (a) with a nucleic acid molecule encoding a carotenoid hydroxylase enzyme of the invention; and (c) growing the transformed host cell of (b) under suitable conditions whereby a hydroxylated carotenoid is produced.

In another embodiment, the invention provides a method of regulating cyclic hydroxylated carotenoid biosynthesis in an organism comprising;

(a) providing a host cell which comprising a carotenoid biosynthetic pathway, said host cell producing a cyclic carotenoid having at least one β-ionone ring;

(b) transforming the host cell of (a) with a nucleic acid molecule encoding a carotenoid hydroxylase enzyme of the invention; and (c) growing the transformed host cell of (b) under conditions whereby the hydroxylated carotenoid biosynthesis is regulated.

BRIEF DESCRIPTION OF THE FIGURES, SEQUENCE DESCRIPTIONS, AND THE BIOLOGICAL DEPOSIT

Figure 1:
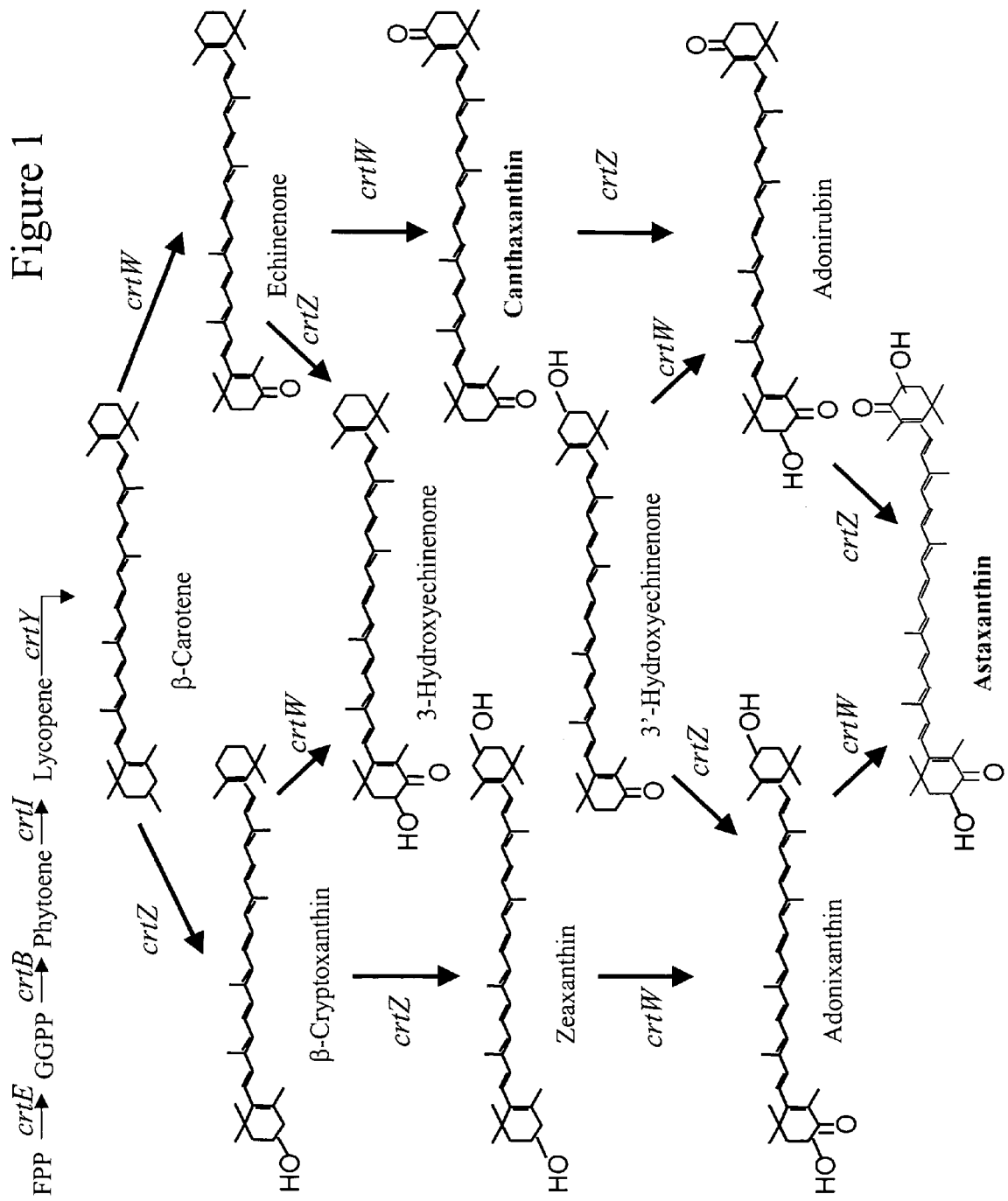
FIG. 1 shows the biosynthetic pathway for the production of astaxanthin from a variety of possible precursors via ketolase and hydroxylase reactions from β-carotene.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleotide sequence of a primer ("HK12") used for 16S rRNA gene sequencing.

SEQ ID NO: 2 is the nucleotide sequence of a primer ("JCR14") used for 16S rRNA gene sequencing.

SEQ ID NO: 3 is the nucleotide sequence of a primer ("JCR15") used for 16S rRNA gene sequencing.

SEQ ID NO: 4 is the nucleotide sequence of the *Brevundimonas vesicularis* DC263 16S rRNA gene.

SEQ ID NO: 5 is the nucleotide sequence of the *Sphingomonas melonis* DC18 16S rRNA gene.

SEQ ID NO: 6 is the nucleotide sequence of the crtEXYIBZ carotenoid synthesis gene cluster from *Enterobacteriaceae* DC260 (U.S. Ser. No. 10/808,979).

SEQ ID NO: 7 is the nucleotide sequence of primer pWEB260F.

SEQ ID NO: 8 is the nucleotide sequence of primer pWEB260R.

SEQ ID NO: 9 is the nucleotide sequence of primer pWEB404F.

SEQ ID NO: 10 is the nucleotide sequence of primer pWEB404R.

SEQ ID NO: 11 is the nucleotide sequence of the crtEidiYIB carotenoid synthesis gene cluster from *Pantoea agglomerans* DC404 (U.S. Ser. No. 10/808,807).

SEQ ID NO: 12 is the nucleotide sequence of the *Brevundimonas vesicularis* DC263 crtW ketolase (U.S. 60/531, 310).

SEQ ID NO: 13 is the nucleotide sequence of the *Sphingomonas melonis* DC18 crtW ketolase (U.S. 60/531,310).

SEQ ID NO: 14 is the nucleotide sequence of primer pEZ263-F.

SEQ ID NO: 15 is the nucleotide sequence of primer pEZ263-R.

SEQ ID NO: 16 is the nucleotide sequence of the *Brevundimonas vesicularis* DC263 crtZ carotenoid hydroxylase.

SEQ ID NO: 17 is the deduced amino acid sequence of the *Brevundimonas vesicularis* DC263 CrtZ carotenoid hydroxylase.

SEQ ID NO: 18 is the amino acid sequence of the *Agrobacterium aurantiacum* CrtZ carotenoid hydroxylase.

SEQ ID NO: 19 is the nucleotide sequence of the *Novosphingobium aromaticivorans* ATCC No. 700278 (GenBank® ZP_00094836.1) CrtZ carotenoid hydroxylase.

SEQ ID NO: 20 is the amino acid sequence of the *Novosphingobium aromaticivorans* ATCC No. 700278 (GenBank® ZP_00094836.1) CrtZ carotenoid hydroxylase.

SEQ ID NO: 21 is the nucleotide sequence of primer crtZ-DC263_F.

SEQ ID NO: 22 is the nucleotide sequence of primer crtZ-DC263_R.

SEQ ID NO: 23 is the nucleotide sequence of primer 41ZSPH_F.

SEQ ID NO: 24 is the nucleotide sequence of primer SPH_ZR.

SEQ ID NO: 25 is the nucleotide sequence of primer crt-260_F.

SEQ ID NO: 26 is the nucleotide sequence of primer crt-260SOE_R.

SEQ ID NO: 27 is the nucleotide sequence of primer crt-260SOE_F.

SEQ ID NO: 28 is the nucleotide sequence of primer crt-260RI_R.

SEQ ID NO: 29 is the nucleotide sequence of primer crt-260RI_F.

SEQ ID NO: 30 is the nucleotide sequence of primer crt-260_R.

SEQ ID NO: 31 is the nucleotide sequence of primer crtW-263_F.

SEQ ID NO: 32 is the nucleotide sequence of primer crtW-263_R.

SEQ ID NO: 33 is the nucleotide sequence of primer crtW-263_F2.

SEQ ID NO: 34 is the nucleotide sequence of primer crtW-263_R2.

SEQ ID NO: 35 is the nucleotide sequence of a first primer used to amplify the phps1 promoter from *Methylomonas* 16a.

SEQ ID NO: 36 is the nucleotide sequence of a second primer used to amplify the phps1 promoter from *Methylomonas* 16a.

SEQ ID NO: 37 is the nucleotide sequence of primer crtW_sphingo_F.

SEQ ID NO: 38 is the nucleotide sequence of primer crtW_sphingo_R.

The following biological deposit has been made under the terms of the Budapest Treaty on the International Recognition of the Deposit of Microorganisms for the Purposes of Patent Procedure:

| Depositor Identification Reference | International Depository Designation | Date of Deposit |
|---|---|---|
| *Methylomonas* 16a | ATCC PTA 2402 | Aug. 22, 2000 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present crtZ genes and their expression product, a carotenoid hydroxylase, are useful for the creation of recombinant organisms that have the ability to produce hydroxylated carotenoid compounds. A novel nucleic acid molecule encoding a carotenoid hydroxylase has been isolated from a bacterial strain denoted as *Brevundimonas vesicularis* DC263. Additionally, a hypothetical protein from *Novosphingobium aromaticivorans* ATCC No. 700278 (GenBank® ZP_00094836.1) has been identified as a carotenoid hydroxylase useful for producing hydroxylated carotenoids using the present methods.

The present crtZ hydroxylase genes were expressed in transgenic microbial hosts engineered to produce suitable substrates (for example, β-carotene or canthaxantin). Functional expression of the genes was measured by the production of hydroxylated carotenoids (for example, zeaxanthin or astaxanthin) in the heterologous hosts.

The carotenoid hydroxylase genes of the present invention may be used in a variety of ways for the production or regulation of cyclic hydroxylated carotenoid compounds. The present crtZ hydroxylase genes can be used for carotenoid production in heterologous hosts having the ability to produce suitable substrates. Additionally, present crtZ hydroxylase genes may be simultaneously coexpressed with one or more divergent carotenoid hydroxylase genes in the heterologous host for optimized production of hydroxylated carotenoids. Simultaneous expression of the present crtZ genes should be possible due to their relatively low to moderate nucleotide sequence identity to other known CrtZ hydroxylases. The relatively low/moderate nucleotide sequence identity increases the likelihood of stable expression of multiple CrtZ hydroxylases in the microbial production host for optimal carotenoid production.

The genes and gene sequences described herein enable one to incorporate the production of hydroxylated carotenoids directly into an industrially suitable microbial host cell. This aspect makes any microbial strain into which these genes are incorporated a more desirable production host. The carotenoids produced can be isolated from the production host for use in a variety of applications, including animal feed. Optionally, the recombinant microbial host cells can be directly incorporated into animal feed (no carotenoid isolation step) due to the presence of carotenoids that are known to add desirable pigmentation and health benefits. Fish (e.g. salmon and trout) and shrimp aquacultures are particularly useful applications for this invention as carotenoid pigmentation is critically important for the value of these organisms (F. Shahidi and J. A. Brown, *Critical Reviews in Food Science*, 38(1):1–67 (1998)). Specifically, the carotenoid astaxanthin is currently used in the aquaculture industry.

In this disclosure, a number of terms and abbreviations are used. The following definitions are provided.

As used herein, "open reading frame" is abbreviated ORF. "Polymerase chain reaction" is abbreviated PCR.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "pBHR-crt1" refers to a β-carotene producing plasmid. The plasmid was constructed by cloning the crtEXYIB carotenoid gene cluster from *Pantoea stewartii* (ATCC 8199) into pBHR1 (MoBioTech, Goettingen, Germany; see WO 02/18617 corresponding to U.S. Ser. No. 09/941,947, hereby incorporated by reference). The resulting plasmid contained the *P. stewartii* gene cluster expressed under the control of the chloramphenicol-resistance gene promoter.

As used herein, the term "pDCQ300" refers to a β-carotene producing plasmid. The plasmid was constructed by cloning the carotenoid gene cluster crtEYIB from *Pantoea stewartii* (ATCC No. 8199) into pTrcHis2-Topo vector (Invitrogen, Carlsbad, Calif.).

As used herein, the term "pDCQ301 refers to a β-carotene producing plasmid constructed by cloning a 4.5 kB EcoRI fragment of pDCQ300 containing the crtEYIB gene cluster into the unique EcoRI site of vector pBHR1 (MoBiTec). In pDCQ301, a unique MfeI site was engineered in the intergenic region of crtE and crtY.

As used herein, the term "pDCQ329" refers to a β-carotene producing plasmid. The plasmid was constructed by cloning the crtEXYIB gene cluster isolated from *Enterobacteriaceae* DC260 into the broad host range vector pBHR1 (U.S. Ser. No. 10/808,979).

As used herein, the term "pDCQ330" refers to a β-carotene producing plasmid. The plasmid was constructed by cloning the crtEidiYIB carotenoid gene cluster from *Pantoea agglomerans* DC404 into a broad host range vector pBHR1 (U.S. Ser. No. 10/808,807 and U.S. 60/527,083).

As used herein, the term "pDCQ340" refers to a plasmid expressing the crtEYIB gene cluster from *Enterobacteriaceae* DC260. The crtX gene in the native gene cluster was deleted. The gene cluster was cloned into vector pBHR1.

As used herein, the term "pDCQ342" refers to a plasmid expressing a crtWEYIB gene cluster. The crtW coding sequence from *Brevundimonas vesicularis* was cloned upstream of the crtEYIB gene cluster from *Enterobacteriaceae* DC260 in pBHR1.

As used herein, the term "pDCQ342TA" refers to a plasmid expressing the crtW gene from *Brevundimonas vesicularis* DC263 cloned into a pTrcHis2-TOPO vector (Invitrogen).

As used herein, the term "pDCQ344" refers to a plasmid expressing the crtZWEYIB gene cluster. The crtZ coding sequence from *Brevundimonas vesicularis* DC263 was cloned upstream of the crtWEYIB gene cluster of pDCQ342, resulting in an astaxanthin-producing plasmid.

As used herein, the term "pDCQ352" refers to a plasmid expressing the crtZ gene from *Brevundimonas vesicularis* DC263 cloned into a pTrcHis2-TOPO vector (Invitrogen).

As used herein, the term "pDCQ363" refers to a plasmid comprised of the phps1 promoter amplified from *Methylomonas* sp. 16a and cloned into pBHR1.

As used herein, the term "pDCQ364" refers to a plasmid comprised of the coding sequence of the crtZ gene from *Novosphingobium aromaticivorans* cloned into plasmid pDCQ363.

As used herein, the term "pDCQ365" refers to a plasmid comprised of the coding sequence of the crtW gene from *Sphingomonas melonis* DC18 cloned into plasmid pDCQ364. The coding sequence of the crtW gene from *Sphingomonas melonis* DC18 and the coding sequence of the crtZ gene from *Novosphingobium aromaticivorans* ATCC No. 700278 were co-expressed as one transcriptional unit under control of the phps1 promoter from *Methylomonas* sp. 16a.

As used herein, the term "pDCQ366" refers to a plasmid comprised of the crtWZ transcriptional unit from pDCQ365 cloned into the β-carotene synthesis plasmid pDCQ330, resulting in a plasmid capable of producing astaxanthin.

As used herein, the term "pDCQ370TA" refers to a plasmid expressing the crtZ gene from *Brevundimonas vesicularis* DC263 cloned into a pTrcHis2-TOPO vector (Invitrogen). It incorporated different restriction sites flanking crtZ gene as in pDCQ352.

As used herein, the term "pTrc-His2-crtZ (Sphingo)" refers to a plasmid expressing the coding sequence of the crtZ gene from *Novosphingobium aromaticivorans* ATCC No. 700278 cloned into a pTrcHis2-TOPO vector (Invitrogen).

As used herein, the term "isoprenoid" or "terpenoid" refers to the compounds are any molecule derived from the isoprenoid pathway including 10 carbon terpenoids and their derivatives, such as carotenoids and xanthophylls.

As used herein, the term "carotenoid" refers to a compound composed of a polyene backbone which is condensed from five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids.

As used herein, the term "carotenoid biosynthetic pathway" refers to those genes comprising members of the upper isoprenoid pathway and/or lower carotenoid biosynthetic pathway.

As used herein, the terms "upper isoprenoid pathway", "isoprenoid pathway", and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "lytB" gene involved in the formation of dimethylallyl diphosphate; the "gcpE" gene involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

As used herein, the terms "lower carotenoid biosynthetic pathway" and "lower pathway" will be used interchangeably and refer to those enzymes which convert FPP to a suite of carotenoids. These include those genes and gene products that are involved in the synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$–$C_{40}$ carotenoids are included within the lower carotenoid biosynthetic pathway. These genes and gene products comprise all of the "crt" genes including, but not limited to: crtM, crtN, crtN2, crtE, crtX, crtY, crtI, crtB, crtZ, crtW, crtO, crtA, crtC, crtD, crtF, and crtU. Finally, the term "lower carotenoid biosynthetic enzyme" is an inclusive term referring to any and all of the enzymes in the lower pathway including, but not limited to: CrtM, CrtN, CrtN2, CrtE, CrtX, CrtY, CrtI, CrtB, CrtZ, CrtW, CrtO, CrtA, CrtC, CrtD, CrtF, and CrtU.

"$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure, having a long central chain of conjugated double bonds, by: (i) hydrogenation (ii) dehydrogenation (iii) cyclization, (iv) oxidation, (v) esterification/glycosylation, or any combination of these processes.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure. Non-limiting examples of $C_{40}$ carotenoids include: phytoene, lycopene, β-carotene, zeaxanthin, astaxanthin, and canthaxanthin.

As used herein, the term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate.

As used herein, the term "Idi" refers to an isopentenyl diphosphate isomerase enzyme (E.C. 5.3.3.2) encoded by the idi gene.

As used herein, the term "CrtY" refers to a lycopene cyclase enzyme encoded by the crtY gene which converts lycopene to β-carotene.

As used herein, the term "CrtI" refers to a phytoene desaturase enzyme encoded by the crtI gene. CrtI converts phytoene into lycopene via the intermediaries of phytofluene, ζ-carotene and neurosporene by the introduction of 4 double bonds.

As used herein, the term "CrtB" refers to a phytoene synthase enzyme encoded by the crtB gene which catalyzes the reaction from prephytoene diphosphate to phytoene.

As used herein, the term "CrtZ" refers to a carotenoid hydroxylase enzyme (e.g. β-carotene hydroxylase), also called 3, 3'β-ionone hydroxylase encoded by the crtZ gene which catalyzes a hydroxylation reaction. The oxidation reaction adds a hydroxyl group to cyclic carotenoids having a β-ionone type ring at 3 and/or 3' position. This reaction converts cyclic carotenoids, such as β-carotene or canthaxanthin, into the hydroxylated carotenoids zeaxanthin or astaxanthin, respectively. Intermediates in the process typically include β-cryptoxanthin and adonirubin. It is known that CrtZ hydroxylases typically exhibit substrate flexibility, enabling production of a variety of hydroxylated carotenoids depending upon the available substrates.

As used herein, the term "CrtW" refers to a β-carotene ketolase enzyme encoded by the crtW gene that catalyzes an oxidation reaction where a keto group is introduced on the β-ionone type ring of cyclic carotenoids. The term "carotenoid ketolase" or "ketolase" refers to the group of enzymes that can add keto groups to the 4 and/or 4' positions of ionone type ring of cyclic carotenoids.

As used herein, the term "CrtX" refers to a zeaxanthin glucosyl transferase enzyme encoded by the crtX gene and which converts zeaxanthin to zeaxanthin-β-diglucoside.

As used herein, the term "hydroxyl group" refers to a univalent radical or group comprised of one oxygen and one hydrogen atom ("—OH").

As used herein, the term "keto group" or "ketone group" will be used interchangeably and refers to a group in which a carbonyl group is bonded to two carbon atoms: $R_2C=O$ (neither R may be H).

As used herein, the term "ketocarotenoid" refers to carotenoids possessing at least on keto group on the ionone ring of a cyclic carotenoid. Examples of ketocarotenoids include canthaxanthin and astaxanthin.

As used herein, the term "cyclic carotenoid" refers to a carotenoid having at least one β-ionone ring or β-ionone ring derivative capable of being hydroxylated by the present CrtZ carotenoid hydroxylases.

As used herein, the terms "carotenoid hydroxylase", "β-carotene hydroxylase", "hydroxylase", and "CrtZ hydroxylase" are used interchangeably and refer to the carotenoid hydroxylase enzyme encoded by a crtZ gene that catalyzes the addition of a hydroxyl group to a β-ionone ring of a cyclic carotenoid.

As used herein, the term "hydroxylated carotenoid" refers to carotenoids possessing at least one hydroxyl group on the ionone ring of a cyclic carotenoid. Examples of hydroxylated carotenoids include zeaxanthin and astaxanthin.

As used herein, "substantially similar" refers to nucleic acid molecules wherein changes in one or more nucleotide bases results in substitution of one or more amino acids, but do not affect the functional properties of the protein encoded by the DNA sequence. "Substantially similar" also refers to nucleic acid molecules wherein changes in one or more nucleotide bases does not affect the ability of the nucleic acid molecule to mediate alteration of gene expression by antisense or co-suppression technology. "Substantially similar" also refers to modifications of the nucleic acid molecules of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. Preferred substantially similar nucleic acid molecules of the instant invention are those nucleic acid molecules whose DNA sequences are at least 80% identical to the DNA sequence of the nucleic acid molecules reported herein. More preferred nucleic acid molecules are at least 90% identical to the DNA sequence of the nucleic acid molecules reported herein. Most preferred are nucleic acid molecules that are at least 95% identical to the DNA sequence of the nucleic acid molecules reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (hereinafter "Maniatis"). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Maniatis, supra, 9.50–9.51). For hybridizations with shorter nucleic acids, i.e., oligonucleotides, the position of mismatches becomes more important, and the length of the oligonucleotide determines its specificity (see Maniatis, supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

As used herein, the phrase "substantial portion" is used to describe an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.*, 215:403–410 (1993)). In general, a sequence of about ten or more contiguous amino acids or about thirty or more nucleotides is necessary in order to putatively identify a polypeptide or nucleic acid sequence as homologous to a known protein or gene. Moreover, with respect to nucleotide sequences, gene specific oligonucleotide probes comprising about 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of about 12–15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.) or the AlignX program of Vector NTI v. 7.0 (Informax, Inc., Bethesda, Md.). Multiple alignment of the sequences can be performed using the Clustal method of alignment (Higgins and Sharp, *CABIOS*, 5:151–153 (1989)) with the default parameters (GAP PENALTY=10, GAP LENGTH PENALTY=10). Default parameters for pairwise alignments using the Clustal method are typically KTUPLE 1, GAP PENALTY=3, WINDOW=5 and DIAGONALS SAVED=5.

Suitable nucleic acid molecules (isolated polynucleotides of the present invention) encode polypeptides that are at least about 80% identical to the amino acid sequences reported herein. More preferred nucleic acid molecules encode amino acid sequences that are about 90% identical to the amino acid sequences reported herein. Even more preferred nucleic acid molecules encode amino acid sequences that are at least about 95% identical to the amino acid sequences reported herein. Suitable nucleic acid molecules of the present invention not only have the above homologies, but also typically encode a polypeptide having about 161 amino acids.

As used herein, the terms "divergent gene", "divergent hydroxylase", and "divergent sequence" are used interchangeable and refer to the lack of nucleic acid molecule sequence identity among CrtZ hydroxylases. Nucleotide sequence comparisons between 2 or more crtZ genes allows classification of the relationship(s) as to the relative degree of sequence identity. Simultaneous expression of highly homologous (i.e. having high nucleotide sequence identity) genes tends to result in genetic instability. Expression of moderately or highly divergent genes is likely to result in stable coexpression. Preferred crtZ hydroxylase genes useful for coexpression are those that share less than about 75% identify when compared by sequence alignment. More preferred crtZ hydroxylase genes for coexpression are those that share less than about 65% identify when compared by sequence alignment. Even more preferred crtZ genes for coexpression are those that share less than about 60% identify when compared by sequence alignment. Most preferred crtZ genes for coexpression are those that share less than about 55% identify when compared by sequence alignment.

As used herein, "codon degeneracy" refers to the nature in the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptides as set forth in SEQ ID NOs: 17 and 20. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid molecule that expresses a specific protein. As used herein, it may or may not including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genetic construct" refers to a series of contiguous nucleic acids useful for modulating the genotype of an organism. Non-limiting examples of genetic constructs include but are not limited to a nucleic acid molecule, and open reading frame, a gene, a plasmid and the like.

"Coding sequence" refers to a DNA sequence that codes for a specific amino acid sequence. As used herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid molecule so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid molecule of the invention. Expression may also refer to translation of mRNA into a polypeptide.

"Transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

"Conjugation" refers to a particular type of transformation in which a unidirectional transfer of DNA (e.g., from a bacterial plasmid) occurs from one bacterium cell (i.e., the "donor") to another (i.e., the "recipient"). The process involves direct cell-to-cell contact.

The term "carbon substrate" refers to a carbon source capable of being metabolized by host organisms of the present invention and particularly carbon sources selected from the group consisting of monosaccharides, disaccharides, polysaccharides, and one-carbon substrates or mixtures thereof. The term "$C_1$ carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide. Particularly preferred are those organisms capable of metabolizing methane and/or methanol.

The term "$C_1$ metabolizer" refers to a microorganism that has the ability to use a single carbon substrate as its sole source of energy and biomass. $C_1$ metabolizers will typically be methylotrophs and/or methanotrophs. The term "$C_1$ metabolizing bacteria" refers to bacteria that have the ability to use a single carbon substrate as their sole source of energy and biomass. $C_1$ metabolizing bacteria, a subset of $C_1$ metabolizers, will typically be methylotrophs and/or methanotrophs.

The term "methylotroph" means an organism capable of oxidizing organic compounds that do not contain carbon-carbon bonds. Where the methylotroph is able to oxidize $CH_4$, the methylotroph is also a methanotroph. In one aspect, the microbial host cell is a methylotroph grown on methane and/or methanol as a primary carbon source.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus*, and *Methylosinus*. In one aspect, the methanotroph is a high growth methanotrophic bacterial strain grown on methane and/or methanol. In another aspect, the methanotroph is a *Methylomonas* sp. 16a (ATCC PTA-2402) and derivatives thereof.

The term "high growth methanotrophic bacterial strain" refers to a bacterium capable of growth with methane or methanol as the sole carbon and energy source and which possesses a functional Embden-Meyerhof carbon flux pathway, resulting in a high rate of growth and yield of cell mass per gram of $C_1$ substrate metabolized (U.S. Pat. No. 6,689,601). The specific "high growth methanotrophic bacterial strain" described herein is referred to as "*Methylomonas* 16a", "16a" or "*Methylomonas* sp. 16a", which terms are used interchangeably and which refer to the *Methylomonas* strain (*Methylomonas* sp. 16a ATCC PTA-2402) used in the present invention.

As used herein, the term "CrtN1" refers to an enzyme encoded by the crtN1 gene, active in the native carotenoid biosynthetic pathway of *Methylomonas* sp. 16a. This gene is located within an operon comprising crtN2 and ald.

As used herein, the term "ALD" refers to an enzyme encoded by the ald gene, active in the native carotenoid biosynthetic pathway of *Methylomonas* sp. 16a. This gene is located within an operon comprising crtN1 and crtN2.

As used herein, the term "CrtN2" refers to an enzyme encoded by the crtN2 gene, active in the native carotenoid biosynthetic pathway of *Methylomonas* sp. 16a. This gene is located within an operon comprising crtN1 and ald.

As used herein, the term "CrtN3" refers to an enzyme encoded by the crtN3 gene, affecting the native carotenoid biosynthetic of *Methylomonas* sp. 16a. This gene is not located within the crt gene cluster; instead this gene is present in a different location in the *Methylomonas* genome.

As used herein, the term "MWM1200 ($\Delta$crt cluster promoter+$\Delta$crtN3)" or "MWM1200" refers to a mutant strain of *Methylomonas* sp. 16a in which the crt cluster promoter and the crtN3 gene have been disrupted. Disruption of the native $C_{30}$ carotenoid biosynthetic pathway results in suitable background (pigmentless) for engineering $C_{40}$ carotenoid production. The *Methylomonas* MWM1200 strain was previously created and is a suitable carotenoid production host (U.S. Ser. No. 10/997,844; hereby incorporated by reference). The term "pigmentless" or "white mutant" refers to a *Methylomonas* sp. 16a bacterium wherein the native pink pigment (e.g., a $C_{30}$ carotenoid) is not produced. Thus, the bacterial cells appear white in color, as opposed to pink.

The terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol*. 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res*., [Proc. Int. Symp.] (1994), Meeting Date 1992, 111–20. Editor(s): Suhai, Sandor. Publisher: Plenum, New York, N.Y.), Vector NTI (Informax, Bethesda, Md.) and Sequencher™ v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

The present invention provides a newly discovered CrtZ carotenoid hydroxylase isolated from *Brevundimonas vesicularis* DC263 (U.S. Ser. No. 11/015,433). Additionally, the function of a hypothetical protein from *Novosphingobium aromaticivorans* ATCC No. 700728 (GenBank® ZP_00094836.1; SEQ ID NO: 20) has been characterized in the present application as having carotenoid hydroxylase activity. Both carotenoid hydroxylases have been shown to produce hydroxylated carotenoids by the present methods. The present sequence may be used in vitro and in vivo in recombinant hosts for the production of hydroxylated carotenoids from cyclic carotenoid compounds.

Comparison of the *Brevundimonas vesicularis* DC263 crtZ nucleotide base and deduced amino acid sequence to public databases reveals that the most similar known sequence has about 51% identity to the amino acid sequence of reported herein over length of 161 amino acids using the BLOSUM62 matrix of the BLASTP search (Table 3). Pairwise comparison values reported in Table 4 were obtained using Align X in Vector NTI. Accordingly preferred amino acid fragments are at least about 80% identical to the sequences herein, more preferred amino acid sequences are at least about 90% identical to the amino acid fragments reported herein, even more preferred amino acid sequences are at least about 95% identical to the amino acid fragments reported herein, and most preferred are nucleic acid molecules that are at least 99% identical to the amino acid molecules reported herein.

Similarly, the preferred crtZ genes are comprised of a nucleic acid sequences encoding active proteins and which are at least 80% identical to the present nucleic acid sequence of reported herein. More preferred crtZ nucleic acid molecules are at least 90% identical to the nucleic acid sequences herein. Even more preferred crtZ nucleic acid molecules are at least 95% identical to the nucleic acid sequences herein. Most preferred are crtZ nucleic acid molecules that are at least 99% identical to the nucleic acid molecules reported herein.

Isolation of Homologs

The nucleic acid molecules of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad. Sci. USA* 82:1074 (1985)) or strand displacement amplification (SDA, Walker, et al., *Proc. Natl. Acad. Sci. U.S.A*., 89:392 (1992)).

For example, genes encoding similar proteins or polypeptides to those of the instant invention could be isolated directly by using all or a portion of the instant nucleic acid molecules as DNA hybridization probes to screen libraries from any desired bacteria using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, end-labeling techniques, or RNA probes using available in vitro transcription systems. In addition, specific primers can be designed and used to amplify a part of or the full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, "PCR Protocols: Current Methods and Applications", Humania Press, Inc., Totowa, N.J.)

Generally two short segments of the instant sequences may be used in polymerase chain reaction protocols to amplify longer nucleic acid molecules encoding homologous genes from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor of a eukaryotic gene. In the case of microbial genes which lack polyadenylated mRNA, random primers may be used. Random primers may also be useful for amplification from DNA.

Alternatively, the second primer sequence may be based upon sequences derived from the cloning vector. For example, the skilled artisan can follow the RACE protocol (Frohman et al., *Proc. Natl. Acad. Sci. U.S.A*, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci. U.S.A*, 86:5673 (1989); Loh et al., *Science* 243: 217 (1989)).

Alternatively, the present sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A., *Adv. Immunol*, 36:1 (1984); Maniatis, supra).

Recombinant Expression—Microbial

The gene(s) and gene product(s) of the instant sequences may be produced in heterologous host cells, particularly in the cells of microbial hosts. Expression in recombinant microbial hosts may be useful for the expression of various pathway intermediates, for the modulation of pathways already existing in the host, or for the synthesis of new products heretofore not possible using the host.

Preferred heterologous host cells for expression of the instant genes and nucleic acid molecules are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid molecules. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia, Candida, Hansenula*, or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. Preferred bacterial host strains include *Escherichia, Bacillus*, and *Methylomonas*. The most preferred bacterial host strains include *Methylomonas* sp. 16a and mutant derivatives thereof (i.e. mutants derived from *Methylomonas* sp. 16a ATCC PTA-2402).

Microbial expression systems and expression vectors containing regulatory sequences that direct high level expression of foreign proteins are well known to those skilled in the art. Any of these could be used to construct chimeric genes for expression of the present carotenoid hydroxylases. These chimeric genes could then be introduced into appropriate microorganisms via transformation to provide high-level expression of the enzymes Accordingly it is expected, for example, that introduction of chimeric genes encoding the instant bacterial enzymes under the control of the appropriate promoters, will demonstrate increased or altered hydroxylated carotenoid production. It is contemplated that it will be useful to express the instant genes both in natural host cells as well as heterologous host. Introduction of the present crtZ genes into native host will result in altered levels of hydroxylated carotenoid production. Additionally, the present genes may also be introduced into non-native host bacteria where the existing carotenoid pathway may be manipulated.

Specific hydroxylated carotenoids that will be produced by the present invention include, but are not limited to zeaxanthin, astaxanthin, β-cryptoxanthin, 3-hydroxyechinenone, 3'-hydroxyechinenone, adonirubin, adonixanthin, tetrahydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal, and lutein. Of particular interest is the production of astaxanthin and zeaxanthin, the synthesis of which is shown in FIG. 1. The specific substrate for the present CrtZ enzyme is a cyclic carotenoid having at least one β-ionone type ring. Cyclic carotenoids are well known in the art and available commercially. Preferred CrtZ hydroxylase substrates include, but are not limited to β-carotene, canthaxanthin, β-cryptoxanthin, 3-hydroxyechinenone, 3'-hydroxyechinenone, echinenone, adonirubin, γ-carotene, 4-keto-γ-carotene, deoxy-flexixanthin, and α-carotene.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*, and promoters isolated from the nrtA, glnB, moxF, glyoxII, htpG, and hps genes useful for expression in *Methylomonas* (U.S. Ser. No. 10/689,200; hereby incorporated by reference). Additionally, promoters such as the chloramphenicol resistance gene promoter (Pcat) may also be useful for expression in *Methylomonas*.

Termination control regions may also be derived from various genes native to the preferred hosts. Optionally, a termination site may be unnecessary, however, it is most preferred if included.

Knowledge of the sequence of the present gene will be useful in manipulating the carotenoid biosynthetic pathways in any organism having such a pathway and particularly in *Methylomonas* sp. 16a and *Escherichia coli*. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced, specific genes may be upregulated to increase the output of the pathway. For example, additional copies of the targeted genes may be introduced into the host cell on multicopy plasmids such as pBR322. Optionally, multiple genes encoding CrtZ hydroxylases may be chromosomally expressed to increase carotenoid production. However, stable chromosomal expression of multiple crtZ genes generally requires that the coding sequences of the genes used are comprised of nucleotide sequences having low to moderate sequence identity to one another. The present carotenoid hydroxylase genes exhibit relative low to moderate nucleotide sequence identity to all previously reported crtZ genes.

Alternatively, the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell (Hamilton et al., *J. Bacteriol.*, 171:4617–4622 (1989); Balbas et al., *Gene*, 136:211–213 (1993); Gueldener et al., *Nucleic Acids Res.*, 24:2519–2524 (1996); and Smith et al., *Methods Mol. Cell. Biol.*, 5:270–277 (1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., (hereinafter "Brock") or Deshpande, Mukund V., *Appl. Biochem. Biotechnol.*, 36:227 (1992) (hereinafter "Deshpande").

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid molecule in the presence of the transposase, the transposable element will randomly insert into the nucleic acid molecule. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Methylotrophs and *Methylomonas* sp. 16a as Microbial Hosts

Although a number of carotenoids have been produced from recombinant microbial sources (e.g., *E. coli* and *Candida utilis* for production of lycopene (Farmer, W. R. and Liao, L. C., *Biotechnol. Prog.*, 17: 57–61 (2001); Wang C. et al., *Biotechnol Prog.*, 16: 922–926 (2000); Misawa, N. and Shimada, H., *J. Biotechnol.*, 59: 169–181 (1998); Shimada, H. et al. *Appl. Environm. Microbiol.* 64:2676–2680 (1998)); *E. coli, Candida utilis*, and *Pfaffia rhodozyma* for production of β-carotene (Albrecht, M. et al., *Biotechnol. Lett.* 21: 791–795 (1999); Miura, Y. et al., *Appl. Environm. Microbiol.* 64:1226–1229 (1998); U.S. Pat. No. 5,691,190); *E. coli* and *Candida utilis* for production of zeaxanthin (Albrecht, M. et al., supra; Miura, Y. et al., supra); *E. coli* and *Pfaffia rhodozyma* for production of astaxanthin (U.S. Pat. No. 5,466,599; U.S. Pat. No. 6,015,684; U.S. Pat. No. 5,182,208; U.S. Pat. No. 5,972,642); see also: U.S. Pat. No. 5,656,472, U.S. Pat. No. 5,545,816, U.S. Pat. No. 5,530,189, U.S. Pat. No. 5,530,188, U.S. Pat. No. 5,429,939, and U.S. Pat. No. 6,124,113), these methods of producing carotenoids using various combinations of different crt genes suffer from low yields and reliance on relatively expensive feedstocks. Thus, it would be desirable to identify a method that produces higher yields of carotenoids in a microbial host from an inexpensive feedstock, such as methane or methanol.

There are a number of microorganisms that utilize single carbon substrates as their sole energy source. Such microorganisms are referred to herein as "$C_1$ metabolizers". These organisms are characterized by the ability to use carbon substrates lacking carbon to carbon bonds as a sole source of energy and biomass. These carbon substrates include, but are not limited to: methane, methanol, formate, formaldehyde, formic acid, methylated amines (e.g., mono-, di- and trimethyl amine), methylated thiols, carbon dioxide, and various other reduced carbon compounds which lack any carbon-carbon bonds. Preferred substrates include methane and/or methanol.

All $C_1$ metabolizing microorganisms are generally classified as methylotrophs. Methylotrophs may be defined as any organism capable of oxidizing organic compounds that do not contain carbon-carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon-carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds.*, [Int. Symp.], 7th (1993), pp 285–302. Murrell, J. Collin and Don P. Kelly, Eds. Intercept: Andover, UK; Madigan et al., *Brock Biology of Microorganisms*, 8th ed., Prentice Hall: UpperSaddle River, N.J. (1997)).

Obligate methylotrophs are those organisms that are limited to the use of organic compounds that do not contain carbon-carbon bonds for the generation of energy.

Obligate methanotrophs are those obligate methylotrophs that have the distinct ability to oxidize methane.

Additionally, the ability to utilize single carbon substrates is not limited to bacteria but extends also to yeasts and fungi.

A number of yeast genera are able to use single carbon substrates as energy sources in addition to more complex materials (i.e., the methylotrophic yeasts).

Although a large number of these methylotrophic organisms are known, few of these microbes have been successfully harnessed in industrial processes for the synthesis of materials. And, although single carbon substrates are cost-effective energy sources, difficulty in genetic manipulation of these microorganisms as well as a dearth of information about their genetic machinery has limited their use primarily to the synthesis of native products.

Despite these difficulties, many methanotrophs contain an inherent isoprenoid pathway that enables these organisms to synthesize pigments and provides the potential for one to envision engineering these microorganisms for production of various non-endogenous isoprenoid compounds. Since methanotrophs can use single carbon substrates (i.e., methane and/or methanol) as an energy source, it could be possible to produce carotenoids at low cost in these organisms. One such example wherein a methanotroph is engineered for production of β-carotene is described in U.S. Ser. No. 09/941,947; hereby incorporated by reference.

Methods are provided for the expression of genes involved in the biosynthesis of carotenoid compounds in microorganisms that are able to use single carbon substrates as a sole energy source. The host microorganism may be any $C_1$ metabolizer that has the ability to synthesize farnesyl pyrophosphate (FPP) as a metabolic precursor for carotenoids. More specifically, facultative methylotrophic bacteria suitable in the present invention include, but are not limited to *Methylophilus, Methylobacillus, Methylobacterium, Hyphomicrobium, Xanthobacter, Bacillus, Paracoccus, Nocardia, Arthrobacter, Rhodopseudomonas*, and *Pseudomonas*. Specific methylotrophic yeasts useful in the present invention include, but are not limited to: *Candida, Hansenula, Pichia, Torulopsis*, and *Rhodotorula*. Exemplary methanotrophs include, but are not limited to the genera *Methylomonas, Methylobacter, Methylococcus, Methylosinus, Methylocyctis, Methylomicrobium*, and *Methanomonas*.

Of particular interest in the present invention are high growth obligate methanotrophs having an energetically favorable carbon flux pathway. For example, a specific strain of methanotroph having several pathway features that makes it particularly useful for carbon flux manipulation. This strain is known as *Methylomonas* 16a (ATCC PTA 2402) (U.S. Pat. No. 6,689,601). This particular strain and other related methylotrophs are preferred microbial hosts for expression of the gene products of this invention (i.e. useful for the production of $C_{40}$ carotenoids).

An optimized version of *Methylomonas* sp. 16a has been created and designated as *Methylomonas* sp. 16a MWM1200 (U.S. Ser. No. 10/997,844; hereby incorporated by reference). The endogenous $C_{30}$ carotenoid pathway was knocked-out (Δcrt cluster promoter+ΔcrtN3), creating an optimized platform for $C_{40}$ carotenoid production. The deletion of the promoter responsible for expression of the endogenous crt cluster (crtN1-ald-crtN2 cluster) resulted in a non-pigmented strain (the wild type strain is normally pink in color due to its natural production of $C_{30}$ carotenoids). Expression of $C_{40}$ carotenoid biosynthesis genes within this optimized host enables increased production of the desired $C_{40}$ carotenoids.

Transformation of $C_1$ Metabolizing Bacteria

Electroporation has been used successfully for the transformation of: *Methylobacterium extorquens* AM1 (Toyama, H., et al., *FEMS Microbiol. Lett.* 166:1–7 (1998)), *Methylophilus methylotrophus* AS1 (Kim, C. S., and T. K. Wood., *Appl. Microbiol. Biotechnol.* 48:105–108 (1997)), and *Methylobacillus* sp. strain 12S (Yoshida, T. et al., *Biotechnol. Lett.*, 23: 787–791 (2001)). Extrapolation of specific electroporation parameters from one specific $C_1$ metabolizing utilizing organism to another may be difficult.

Bacterial conjugation, relying on the direct contact of donor and recipient cells, is frequently more readily amenable for the transfer of genes into $C_1$ metabolizing bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

1. In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a released 5' end (forming a relaxosome as the intermediate structure); and 4.) Subsequently, a complex of auxiliary proteins assemble at oriT to facilitate the process of DNA transfer.

2. Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving $C_1$ metabolizing bacteria include the work of: Stolyar et al. (*Mikrobiologiya* 64(5): 686–691 (1995)); Motoyama, H. et al. (*Appl. Micro. Biotech.* 42(1): 67–72 (1994)); Lloyd, J. S. et al. (*Archives of Microbiology* 171(6): 364–370 (1999)); and Odom, J. M. et al. (U.S. Ser. No. 10/997,308, U.S. Ser. No. 10/997,844, and U.S. Ser. No. 09/941,947; each hereby incorporated by reference).

Industrial Production

Where commercial production of cyclic hydroxylated carotenoid compounds is desired using the present crtZ genes, a variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system with the exception that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch culturing methods are common and well known in the art and examples may be found in Brock (supra) and Deshpande (supra).

Commercial production of carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1 Compd., [Int. Symp.], 7th (1993), 415–32. Editor(s): Murrell, J. Collin; Kelly, Don P. Publisher: Intercept, Andover, UK). Similarly, various species of Candida will metabolize alanine or oleic acid (Sulter et al., Arch. Microbiol., 153:485–489 (1990)). Hence, it is contemplated that the source of carbon utilized in the present invention may encompass a wide variety of carbon containing substrates and will only be limited by the choice of organism.

Recombinant Expression—Plants

Plants and algae are also known to produce carotenoid compounds. The nucleic acid molecules of the instant invention may be used to create transgenic plants having the ability to express the microbial protein. Preferred plant hosts will be any variety that will support a high production level of the instant proteins. Suitable green plants will include, but are not limited to soybean, rapeseed (Brassica napus, B. campestris), pepper, sunflower (Helianthus annus), cotton (Gossypium hirsutum), corn, tobacco (Nicotiana tabacum), alfalfa (Medicago sativa), wheat (Triticum sp), barley (Hordeum vulgare), oats (Avena sativa, L), sorghum (Sorghum bicolor), rice (Oryza sativa), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but not limited to commercially significant hosts such as Spirulina, Haemotacoccus, and Dunalliela. Production of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention should be capable of promoting expression of the present gene product. High-level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.*, 4:2411–2418 (1985); De Almeida et al., *Mol. Gen. Genetics*, 218:78–86 (1989)). Thus, multiple events must be screened in order to obtain lines displaying the desired expression level and pattern. Such screening may be accomplished by Southern analysis of DNA blots (Southern, *J. Mol. Biol.*, 98:503 (1975)). Northern analysis of mRNA expression (Kroczek, *J. Chromatogr. Biomed. Appl.*, 618 (1–2):133–145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell*, 56:247–253 (1989)), signal sequences or sequences encoding endoplasmic reticulum localization (Chrispeels, J. J., *Ann. Rev. Plant Phys. Plant Mol. Biol.*, 42:21–53 (1991)), or nuclear localization signals (Raikhel, N., *Plant Phys.*, 100: 1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotides may be used to produce gene products having enhanced or altered activity. Various methods are known for mutating a native gene sequence to produce a gene product with altered or enhanced activity including but not limited to error-prone PCR (Melnikov et al., *Nucleic Acids Research*, Vol. 27(4): 1056–1062 (1999)); site-directed mutagenesis (Coombs et al., *Proteins*, 259–311, Editor(s): Angeletti, Ruth Hogue. Publisher: Academic, San Diego, Calif. (1998)) and "gene shuffling" (U.S. Pat. No. 5,605,793; U.S. Pat. No. 5,811,238; U.S. Pat. No. 5,830,721; U.S. Pat. No. 5,837,458; and U.S. Ser. No. 10/374,366, hereby incorporated by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments that are not hybridizable to the instant sequence may also be added. Typically, these additional fragment populations are added in about 10 to 20 fold excess by weight as compared to the total nucleic acid. Normally if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP, and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably, the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol (Maniatis, supra).

Furthermore, a hybrid protein can be assembled by fusion of functional domains using the gene shuffling (exon shuffling) method (Nixon et al., *Proc. Natl. Acad. Sci. U.S.A*, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

Genes Involved in Carotenoid Production.

The enzyme pathway involved in the biosynthesis of carotenoids can be conveniently viewed in two parts, the upper isoprenoid pathway providing for the conversion of pyruvate and glyceraldehyde-3-phosphate to farnesyl pyrophosphate (FPP) and the lower carotenoid biosynthetic pathway, which provides for the synthesis of phytoene and all subsequently produced carotenoids. The upper pathway is ubiquitous in many non-carotenogenic microorganisms and in these cases it will only be necessary to introduce genes that comprise the lower pathway for the biosynthesis of the desired carotenoid. The key division between the two pathways concerns the synthesis of farnesyl pyrophosphate. Where FPP is naturally present, only elements of the lower carotenoid pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common C5 isoprene sub-unit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135–140 (1993); Rohmer et al., *Biochem.*, 295:517–524 (1993); Schwender et al., *Biochem.*, 316:73–80 (1996); and Eisenreich et al., *Proc. Natl. Acad. Sci. USA*, 93:6431–6436 (1996)).

Many steps in the mevalonate-independent isoprenoid pathway are known. For example, the initial steps of the alternate pathway leading to the production of IPP have been studied in *Mycobacterium tuberculosis* by Cole et al. (*Nature*, 393:537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr (ispC). 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP. Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. YchB phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). YgbB converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663).

The enzymes encoded by the gcpE (ispG) and lytB (ispH) genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene. However, this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate. This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

Genes encoding elements of the upper pathway are known from a variety of plant, animal, and bacterial sources, as shown in Table 1.

TABLE 1

Sources of Genes Encoding the Upper Isoprenoid Pathway

| Gene | GenBank Accession Number and Source Organism |
|---|---|
| dxs (D-1-deoxyxylulose 5-phosphate synthase) | AF035440, *Escherichia coli*<br>Y18874, *Synechococcus* PCC6301<br>AB026631, *Streptomyces* sp. CL190<br>AB042821, *Streptomyces griseolosporeus*<br>AF111814, *Plasmodium falciparum*<br>AF143812, *Lycopersicon esculentum*<br>AJ279019, *Narcissus pseudonarcissus*<br>AJ291721, *Nicotiana tabacum* |
| dxr (ispC) (1-deoxy-D-xylulose 5-phosphate reductoisomerase) | AB013300, *Escherichia coli*<br>AB049187, *Streptomyces griseolosporeus*<br>AF111813, *Plasmodium falciparum*<br>AF116825, *Mentha x piperita*<br>AF148852, *Arabidopsis thaliana*<br>AF182287, *Artemisia annua*<br>AF250235, *Catharanthus roseus*<br>AF282879, *Pseudomonas aeruginosa*<br>AJ242588, *Arabidopsis thaliana*<br>AJ250714, *Zymomonas mobilis* strain ZM4<br>AJ292312, *Klebsiella pneumoniae*,<br>AJ297566, *Zea mays* |
| ygbP (ispD) (2-C-methyl-D-erythritol 4-phosphate cytidylyltransferase) | AB037876, *Arabidopsis thaliana*<br>AF109075, *Clostridium difficile*<br>AF230736, *Escherichia coli*<br>AF230737, *Arabidopsis thaliana* |
| ychB (ispE) (4-diphosphocytidyl-2-C-methyl-D-erythritol kinase) | AF216300, *Escherichia coli*<br>AF263101, *Lycopersicon esculentum*<br>AF288615, *Arabidopsis thaliana* |
| ygbB (ispF) (2-C-methyl-D-erythritol 2,4-cyclodiphosphate synthase) | AB038256, *Escherichia coli mecs* gene<br>AF230738, *Escherichia coli*<br>AF250236, *Catharanthus roseus* (MECS)<br>AF279661, *Plasmodium falciparum*<br>AF321531, *Arabidopsis thaliana* |
| gcpE (ispG) (1-hydroxy-2-methyl-2-(E)-butenyl 4-diphosphate synthase) | O67496, *Aquifex aeolicus*<br>P54482, *Bacillus subtilis*<br>Q9pky3, *Chlamydia muridarum*<br>Q9Z8H0, *Chlamydophila pneumoniae*<br>O84060, *Chlamydia trachomatis*<br>P27433, *Escherichia coli*<br>P44667, *Haemophilus influenzae*<br>Q9ZLL0, *Helicobacter pylori* J99<br>O33350, *Mycobacterium tuberculosis*<br>S77159, *Synechocystis* sp.<br>Q9WZZ3, *Thermotoga maritima*<br>O83460, *Treponema pallidum*<br>Q9JZ40, *Neisseria meningitidis*<br>Q9PPM1, *Campylobacter jejuni*<br>Q9RXC9, *Deinococcus radiodurans*<br>AAG07190, *Pseudomonas aeruginosa*<br>Q9KTX1, *Vibrio cholerae* |

TABLE 1-continued

Sources of Genes Encoding the Upper Isoprenoid Pathway

| Gene | GenBank Accession Number and Source Organism |
|---|---|
| IytB (ispH) | AF027189, *Acinetobacter* sp. BD413<br>AF098521, *Burkholderia pseudomallei*<br>AF291696, *Streptococcus pneumoniae*<br>AF323927, *Plasmodium falciparum* gene<br>M87645, *Bacillus subtillis*<br>U38915, *Synechocystis* sp.<br>X89371, *C. jejunisp* O67496 |
| IspA (FPP synthase) | AB003187, *Micrococcus luteus*<br>AB016094, *Synechococcus elongatus*<br>AB021747, *Oryza sativa* FPPS1 gene for farnesyl diphosphate synthase<br>AB028044, *Rhodobacter sphaeroides*<br>AB028046, *Rhodobacter capsulatus*<br>AB028047, *Rhodovulum sulfidophilum*<br>AF112881 and AF136602, *Artemisia annua*<br>AF384040, *Mentha* x *piperita*<br>D00694, *Escherichia coli*<br>D13293, *B. stearothermophilus*<br>D85317, *Oryza sativa*<br>X75789, *A. thaliana*<br>Y12072, *G. arboreum*<br>Z49786, *H. brasiliensis*<br>U80605, *Arabidopsis thaliana* farnesyl diphosphate synthase precursor (FPS1) mRNA, complete cds<br>X76026, *K. lactis* FPS gene for farnesyl diphosphate synthetase, QCR8 gene for bc1 complex, subunit VIII<br>X82542, *P. argentatum* mRNA for farnesyl diphosphate synthase (FPS1)<br>X82543, *P. argentatum* mRNA for farnesyl diphosphate synthase (FPS2)<br>BC010004, *Homo sapiens*, farnesyl diphosphate synthase (farnesyl pyrophosphate synthetase, dimethylallyltranstransferase, geranyltranstransferase), clone MGC 15352 IMAGE, 4132071, mRNA, complete cds<br>AF234168, *Dictyostelium discoideum* farnesyl diphosphate synthase (Dfps)<br>L46349, *Arabidopsis thaliana* farnesyl diphosphate synthase (FPS2) mRNA, complete cds<br>L46350, *Arabidopsis thaliana* farnesyl diphosphate synthase (FPS2) gene, complete cds<br>L46367, *Arabidopsis thaliana* farnesyl diphosphate synthase (FPS1) gene, alternative products, complete cds<br>M89945, Rat farnesyl diphosphate synthase gene, exons 1-8<br>NM_002004, *Homo sapiens* farnesyl diphosphate synthase (farnesyl pyrophosphate synthetase, dimethylallyltranstransferase, geranyltranstransferase) (FDPS), mRNA<br>U36376, *Artemisia annua* farnesyl diphosphate synthase (fps1) mRNA, complete cds<br>XM_001352, *Homo sapiens* farnesyl diphosphate synthase (farnesyl pyrophosphate synthetase, dimethylallyltranstransferase, geranyltranstransferase) (FDPS), mRNA<br>XM_034497, *Homo sapiens* farnesyl diphosphate synthase (farnesyl pyrophosphate synthetase, dimethylallyltranstransferase, geranyltranstransferase) (FDPS), mRNA<br>XM_034498, *Homo sapiens* farnesyl diphosphate synthase (farnesyl pyrophosphate synthetase, dimethylallyltranstransferase, geranyltranstransferase) (FDPS), mRNA<br>XM_034499, *Homo sapiens* farnesyl diphosphate synthase (farnesyl pyrophosphate synthetase, dimethylallyltranstransferase, geranyltranstransferase) (FDPS), mRNA<br>XM_0345002, *Homo sapiens* farnesyl diphosphate synthase (farnesyl pyrophosphate synthetase, dimethylallyltranstransferase, geranyltranstransferase) (FDPS), mRNA |

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the first step in the lower carotenoid biosynthetic pathway is considered to begin with the prenyltransferase reaction converting farnesyl pyrophosphate (FPP) to geranylgeranyl pyrophosphate (GGPP). The gene crtE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

Lycopene is produced from phytoene through four sequential dehydrogenation reactions by the removal of eight atoms of hydrogen, catalyzed by the gene crtI (encoding phytoene desaturase). Intermediaries in this reaction are phytofluene, zeta-carotene, and neurosporene.

Lycopene cyclase (crtY) converts lycopene to β-carotene. However, additional genes may be used to create a variety of other carotenoids. For example, β-carotene is converted to zeaxanthin via a hydroxylation reaction resulting from the activity of β-carotene hydroxylase (encoded by the crtZ gene). β-cryptoxanthin is an intermediate in this reaction.

β-carotene can be converted to canthaxanthin by β-carotene ketolase encoded by either the crtW, bkt or crtO genes. Echinenone is typically an intermediate in this reaction. Canthaxanthin can then be converted to astaxanthin by β-carotene hydroxylase encoded by the crtZ gene. Adonbirubrin is an intermediate in this reaction.

Zeaxanthin can be converted to zeaxanthin-β-diglucoside. This reaction is catalyzed by zeaxanthin glucosyl transferase (crtX).

Genes encoding elements of the lower carotenoid biosynthetic pathway are known from a variety of plant, animal, and bacterial sources, as shown in Table 2.

TABLE 2

Sources of Genes Encoding the Lower Carotenoid Biosynthetic Pathway

| Gene | GenBank Accession Number and Source Organism |
|---|---|
| crtE (GGPP Synthase) | AB000835, *Arabidopsis thaliana*<br>AB016043 and AB019036, *Homo sapiens*<br>AB016044, *Mus musculus*<br>AB027705 and AB027706, *Daucus carota*<br>AB034249, *Croton sublyratus*<br>AB034250, *Scoparia dulcis*<br>AF020041, *Helianthus annuus*<br>AF049658, *Drosophila melanogaster* signal recognition particle 19 kDa protein (srp19) gene, partial sequence; and geranylgeranyl pyrophosphate synthase (quemao) gene, complete cds<br>AF049659, *Drosophila melanogaster* geranylgeranyl pyrophosphate synthase mRNA, complete cds<br>AF139916, *Brevibacterium linens*<br>AF279807, *Penicillium paxilli* geranylgeranyl pyrophosphate synthase (ggs1) gene, complete<br>AF279808, *Penicillium paxilli* dimethylallyl tryptophan synthase (paxD) gene, partial cds; and cytochrome P450 monooxygenase (paxQ), cytochrome P450 monooxygenase (paxM), geranylgeranyl pyrophosphate synthase (paxG), PaxU (paxU), and metabolite transporter (paxT) genes, complete cds<br>AJ010302, *Rhodobacter sphaeroides*<br>AJ133724, *Mycobacterium aurum* |

TABLE 2-continued

Sources of Genes Encoding the Lower Carotenoid Biosynthetic Pathway

| Gene | GenBank Accession Number and Source Organism |
|---|---|
| | AJ276129, *Mucor circinelloides* f. *lusitanicus* carG gene for geranylgeranyl pyrophosphate synthase, exons 1-6 |
| | D85029, *Arabidopsis thaliana* mRNA for geranylgeranyl pyrophosphate synthase, partial cds |
| | L25813, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | U15778, *Lupinus albus* geranylgeranyl pyrophosphate synthase (ggps1) mRNA, complete cds |
| | U44876, *Arabidopsis thaliana* pregeranylgeranyl pyrophosphate synthase (GGPS2) mRNA, complete cds |
| | X92893, *C. roseus* |
| | X95596, *S. griseus* |
| | X98795, *S. alba* |
| | Y15112, *Paracoccus marcusii* |
| crtX (Zeaxanthin glucosylase) | D90087, *E. uredovora* |
| | M87280 and M90698, *Pantoea agglomerans* |
| crtY (Lycopene-β-cyclase) | AF139916, *Brevibacterium linens* |
| | AF152246, *Citrus x paradisi* |
| | AF218415, *Bradyrhizobium* sp. ORS278 |
| | AF272737, *Streptomyces griseus* strain IFO13350 |
| | AJ133724, *Mycobacterium aurum* |
| | AJ250827, *Rhizomucor circinelloides* f. *lusitanicus* carRP gene for lycopene cyclase/phytoene synthase, exons 1–2 |
| | AJ276965, *Phycomyces blakesleeanus* carRA gene for phytoene synthase/lycopene cyclase, exons 1-2 |
| | D58420, *Agrobacterium aurantiacum* |
| | D83513, *Erythrobacter longus* |
| | L40176, *Arabidopsis thaliana* lycopene cyclase (LYC) mRNA, complete cds |
| | M87280, *Pantoea agglomerans* |
| | U50738, *Arabodopsis thaliana* lycopene epsilon cyclase mRNA, complete cds |
| | U50739, *Arabidosis thaliana* lycopene β cyclase mRNA, complete cds |
| | U62808, *Flavobacterium* ATCC21588 |
| | X74599, *Synechococcus* sp. lcy gene for lycopene cyclase |
| | X81787, *N. tabacum* CrtL-1 gene encoding lycopene cyclase |
| | X86221, *C. annuum* |
| | X86452, *L. esculentum* mRNA for lycopene β-cyclase |
| | X95596, *S. griseus* |
| | X98796, *N. pseudonarcissus* |
| crtI (Phytoene desaturase) | AB046992, *Citrus unshiu* CitPDS1 mRNA for phytoene desaturase, complete cds |
| | AF039585, *Zea mays* phytoene desaturase (pds1) gene promoter region and exon 1 |
| | AF049356, *Oryza sativa* phytoene desaturase precursor (Pds) mRNA, complete cds |
| | AF139916, *Brevibacterium linens* |
| | AF218415, *Bradyrhizobium* sp. ORS278 |
| | AF251014, *Tagetes erecta* |
| | AF364515, *Citrus x paradisi* |
| | D58420, *Agrobacterium aurantiacum* |
| | D83514, *Erythrobacter longus* |
| | L16237, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | L39266, *Zea mays* phytoene desaturase (Pds) mRNA, complete cds |
| | M64704, Soybean phytoene desaturase |
| | M88683, *Lycopersicon esculentum* phytoene desaturase (pds) mRNA, complete cds |
| | S71770, carotenoid gene cluster |
| | U37285, *Zea mays* |
| | U46919, *Solanum lycopersicum* phytoene desaturase (Pds) gene, partial cds |
| | U62808, *Flavobacterium* ATCC21588 |
| | X55289, *Synechococcus* pds gene for phytoene desaturase |
| | X59948, *L. esculentum* |
| | X62574, *Synechocystis* sp. pds gene for phytoene desaturase |
| | X68058, *C. annuum* pds1 mRNA for phytoene desaturase |
| | X71023, *Lycopersicon esculentum* pds gene for phytoene desaturase |
| | X78271, *L. esculentum* (Ailsa Craig) PDS gene |
| | X78434, *P. blakesleeanus* (NRRL1555) carB gene |
| | X78815, *N. pseudonarcissus* |
| | X86783, *H. pluvialis* |
| | Y14807, *Dunaliella bardawil* |
| | Y15007, *Xanthophyllomyces dendrorhous* |
| | Y15112, *Paracoccus marcusii* |
| | Y15114, *Anabaena* PCC7210 crtP gene |
| | Z11165, *R. capsulatus* |
| crtB (Phytoene synthase) | AB001284, *Spirulina platensis* |
| | AB032797, *Daucus carota* PSY mRNA for phytoene synthase, complete cds |
| | AB034704, *Rubrivivax gelatinosus* |
| | AB037975, *Citrus unshiu* |
| | AF009954, *Arabidopsis thaliana* phytoene synthase (PSY) gene, complete cds |
| | AF139916, *Brevibacterium linens* |
| | AF152892, *Citrus x paradisi* |
| | AF218415, *Bradyrhizobium* sp. ORS278 |
| | AF220218, *Citrus unshiu* phytoene synthase (Psy1) mRNA, complete cds |
| | AJ010302, *Rhodobacter* |
| | AJ133724, *Mycobacterium aurum* |
| | AJ278287, *Phycomyces blakesleeanus* carRA gene for lycopene cyclase/phytoene synthase, |
| | AJ304825, *Helianthus annuus* mRNA for phytoene synthase (psy gene) |
| | AJ308385, *Helianthus annuus* mRNA for phytoene synthase (psy gene) |
| | D58420, *Agrobacterium aurantiacum* |
| | L23424, *Lycopersicon esculentum* phytoene synthase (PSY2) mRNA, complete cds |
| | L25812, *Arabidopsis thaliana* |
| | L37405, *Streptomyces griseus* geranylgeranyl pyrophosphate synthase (crtB), phytoene desaturase (crtE) and phytoene synthase (crtI) genes, complete cds |
| | M38424, *Pantoea agglomerans* phytoene synthase (crtE) gene, complete cds |
| | M87280, *Pantoea agglomerans* |
| | S71770, Carotenoid gene cluster |
| | U32636, *Zea mays* phytoene synthase (Y1) gene, complete cds |
| | U62808, *Flavobacterium* ATCC21588 |
| | U87626, *Rubrivivax gelatinosus* |
| | U91900, *Dunaliella bardawil* |
| | X52291, *Rhodobacter capsulatus* |
| | X60441, *L. esculentum* GTom5 gene for phytoene synthase |
| | X63873, *Synechococcus* PCC7942 pys gene for phytoene synthase |
| | X68017, *C. annuum* psy1 mRNA for phytoene synthase |
| | X69172, *Synechocystis* sp. pys gene for phytoene synthase |
| | X78814, *N. pseudonarcissus* |

TABLE 2-continued

Sources of Genes Encoding the Lower Carotenoid Biosynthetic Pathway

| Gene | GenBank Accession Number and Source Organism |
|---|---|
| crtZ (β-carotene hydroxylase) | D58420, *Agrobacterium aurantiacum*<br>D58422, *Alcaligenes* sp.<br>D90087, *E. uredovora*<br>M87280, *Pantoea agglomerans*<br>U62808, *Flavobacterium* ATCC21588<br>Y15112, *Paracoccus marcusii* |
| crtW (β-carotene ketolase) | AF218415, *Bradyrhizobium* sp. ORS278<br>D45881, *Haematococcus pluvialis*<br>D58420, *Agrobacterium aurantiacum*<br>D58422, *Alcaligenes* sp.<br>X86782, *H. pluvialis*<br>Y15112, *Paracoccus marcusii* |

Preferred sources of the non-crtZ carotenoid genes are from *Pantoea stewartii* (ATCC 8199; WO 02/079395), *Pantoea agglomerans* DC404 (U.S. Ser. No. 10/808,807; hereby incorporated by reference), *Enterobacteriaceae* DC260 (U.S. Ser. No. 10/808,979; hereby incorporated by reference), *Brevundimonas vesicularis* DC263 (U.S. Ser. No. 11/015,433; hereby incorporated by reference), and *Sphingomonas melonis* DC18 (U.S. Ser. No. 11/015,433; hereby incorporated by reference). The preferred source of crtZ gene for the production of hydroxylated carotenoids using the present method is from *Brevundimonas vesicularis* DC263 (SEQ ID NO: 16) or *Novosphingobium aromaticivorans* ATCC No. 700278 (SEQ ID NO: 19).

By using various combinations of the genes presented in Table 2 and the preferred crtZ genes of the present invention, numerous different carotenoids and carotenoid derivatives could be made using the methods of the present invention, provided that sufficient sources of FPP are available in the host organism. For example, the gene cluster crtEXYIB enables the production of β-carotene. Addition of the crtZ to crtEXYIB enables the production of zeaxanthin.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Maniatis (supra) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)), or in Brock (supra) or Deshpande (supra). All reagents, restriction enzymes and materials used for the growth and maintenance of bacterial cells were obtained from Aldrich Chemicals (Milwaukee, Wis.), DIFCO Laboratories/BD Diagnostics (Sparks, Md.), Promega (Madison, Wis.), New England Biolabs (Beverly, Mass.), GIBCO/BRL Life Technologies (Carlsbad, Calif.), or Sigma Chemical Company (St. Louis, Mo.) unless otherwise specified.

Sequence editing and alignment was performed using Sequencher program. Search of sequences in the nr databases was performed with BLASTP using BLOSUM62 matrix. Pairwise sequence alignments of nucleotide and amino acid sequences were performed using AlignX in Vector NTI. In any case where program parameters were not prompted for, in these or any other programs, default values were used.

The meaning of abbreviations is as follows: "h" means hour(s), "min" means minute(s), "sec" means second(s), "d" means day(s), "mL" means milliliters, "μL" mean microliters, "L" means liters, "g" means grams, "mg" means milligrams, "μg" means micrograms, and "ppm" means parts per million.

Example 1

Isolation and Characterization of Carotenoid-Producing Bacterial Strains

This example describes isolation of two bacterial strains *Brevundimonas vesicularis* DC263 and *Sphingomonas melonis* DC18 and preliminary analysis of their native carotenoids.

Strain Isolation and Typing

To isolate novel carotenoid producing bacterial strains, pigmented microbes were isolated from a collection of environmental samples. Approximately 1 g of surface soil from a yard in Wilmington, Del. was resuspended in 10 mL of tap water. A 10-μL loopful of the water was streaked onto Luria-Broth (LB) plates and the plates were incubated at 30° C. Pigmented bacteria with diverse colony appearances were picked and streaked twice to homogeneity on LB plates and incubated at 30° C. From these colonies, one which formed orange-pink colonies was designated as strain DC263 (U.S. Ser. No. 11/015,433). Strain DC18 was isolated from a Pennsylvania stream. Serial dilutions ($10^{-2}$, $10^{-4}$ and $10^{-6}$) of the aqueous sample were plated onto large 245×245 mm 15% agar plates with basal medium enriched with tryptone and yeast. The components of the basal medium (per liter) were: $NH_4Cl$ 0.8 g, $KH_2PO_4$ 0.5 g, $MgCl_26H_2O$ 0.2 g, $CaCl_22H_2O$ 0.1 g, $NaNO_3$ 1.3 g, and $Na_2SO_4$ 0.5 g. The components of the stock solution 1 were (per liter): nitrilotriacetic acid 12.8 g, $FeCl_2.4H_2O$ 0.3 g, $CuCl_2.2H_2O$ 0.0254 g, $MnCl_2.4H_2O$ 0.1 g, $CoCl_2.6H_2O$ 0.312 g, $ZnCl_2$ 0.1 g, $H_3BO_3$ 0.01 g, $Na_2MoO_4.2H_2O$ 0.01 g, and $NiCl_2.6H_2O$ 0.184 g. Ten milliliters of stock solution 1 was added per 1 litre of the basal medium. The medium was supplemented with tryptone at concentration 10 g/L and yeast extract 5 g/L. Media pH was adjusted to 7. The plates were incubated at room temperature and single colonies were streaked twice onto the same plates. One strain was selected which formed orange colonies and was designated as strain DC18 (U.S. Ser. No. 11/015,433).

16S rRNA gene sequencing was performed with DC263 and DC18. Specifically, the 16S rRNA gene of the strain was amplified by PCR using primers HK12: 5'-GAGTTTGATC-CTGGCTCAG-3' (SEQ ID NO: 1) and JCR14: 5'-ACGGGCGGTGTGTAC-3' (SEQ ID NO: 2). The amplified 16S rRNA genes were purified using a QIAquick PCR Purification Kit according to the manufacturer's instructions (Qiagen, Valencia, Calif.) and sequenced on an automated ABI sequencer (Applied Biosystems, Foster City, Calif.). The sequencing reactions were initiated with primers HK12, JCR14, and JCR15: 5'-GCCAGCAGCCGCGGTA-3' (SEQ ID NO: 3). The assembled 1268 bp 16S rRNA gene sequence (SEQ ID NO: 4) of DC263 and 1291 bp 16S rRNA gene sequence (SEQ ID NO: 5) of DC18 were used as the query sequence for a BLASTN search (Altschul et al., *Nucleic Acids Res.*, 25:3389–3402(1997)) against GenBank®. The 16S rRNA gene sequence of DC263 showed homology to those of *Brevundimonas* strains, with the top hit as 99% identical to *Brevundimonas vesicularis*. This strain was thus designated as *Brevundimonas vesicularis* DC263. The 16S rRNA gene sequence of DC18 showed homology to those of *Sphingomonas* strains, with the top hit as 98% identical to *Sphingomonas melonis*. This strain was thus designated as *Sphingomonas melonis* DC18.

Carotenoid Analysis

*Brevundimonas vesicularis* DC263 was grown in 100 mL LB. *Sphingomonas melonis* DC18 was grown in 100 mL of the same medium as described for the strain isolation. Both strains were grown at 30° C. shaking overnight. Cells were pelleted by centrifugation at 4000 g for 15 min, and the cell pellets were extracted with 10 mL acetone. The extraction was dried under nitrogen and redissolved in 1–2 mL of acetone. The extraction was filtered with an Acrodisc® CR25 mm syringe filter (Pall Corporation, Ann Arbor, Mich.). It was then concentrated in 0.1 mL 10% acetone+ 90% acetonitrile for HPLC analysis using an Agilent Series 1100 LC/MSD SI (Agilent, Foster City, Calif.).

Samples (20 µL) were loaded onto a 150 mm×4.6 mm ZORBAX C18 (3.5 µm particles) column (Agilent Technologies, Inc.). The column temperature was kept at 40° C. The flow rate was 1 mL/min, while the solvent running program used was 0–2 min: 95% Buffer A and 5% Buffer B;

2–10 min: linear gradient from 95% Buffer A and 5% Buffer B to 60% Buffer A and 40% Buffer B;

10–12 min: linear gradient from 60% Buffer A and 40% Buffer B to 50% Buffer A and 50% Buffer B;

12–18 min: 50% Buffer A and 50% Buffer B; and,

18–20 min: 95% Buffer A and 5% Buffer B.

Buffer A was 95% acetonitrile and 5% dH$_2$O; Buffer B was 100% tetrahydrofuran.

Figure 2:
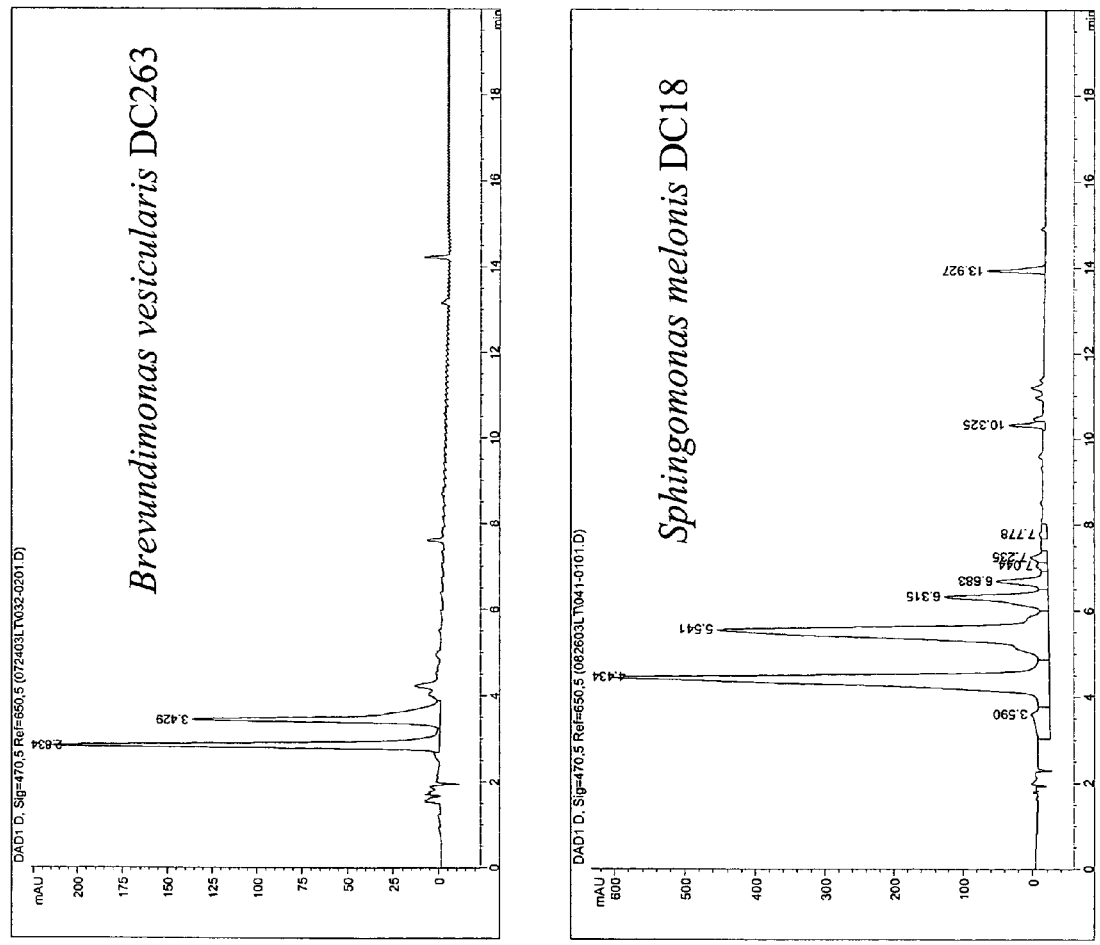
FIG. 2 shows the HPLC analysis of native carotenoids produced by *Brevundimonas vesicularis* DC263 and *Sphingomonas melonis* DC18.

FIG. 2 shows the HPLC profiles of the carotenoids produced in DC263 and DC18, respectively. LC-MS analyses determined that the molecular weight of the major carotenoid in DC263 to be 628, and the molecular weight of the major carotenoid in DC18 to be 614. Based on the HPLC elution times, the absorption spectra, and the molecular weight, the major carotenoid in DC263 was predicted to be tetrahydroxy-β,β'-caroten-4,4'-dione. The major carotenoid in DC18 was predicted to be tetrahydroxy-β,β'-caroten-4-one. The properties determined for the major carotenoid in DC263 and DC18 were consistent with those reported in the literature for these carotenoids (Yokoyama et al., *Biosci. Biotech. Biochem.*, 60:200–203 (1996); Kleinig et al, *Helvetica Chimica Acta*, 60:254–258 (1977)).

Example 2

Construction of β-Carotene Synthesis Plasmids

Two β-carotene synthesis plasmids were used in this application. Plasmid pDCQ329 was used as a reporter plasmid for screening of small insert library to clone the hydroxylase gene(s). It contained the crtEXYIB gene cluster isolated from a carotenoid-producing strain DC260 (U.S. Ser. No. 10/808,979). Isolation of the carotenoid gene cluster from *Enterobacteriaceae* strain DC260 and construction of plasmid pDCQ329 were previously described in U.S. Ser. No. 10/808,979; hereby incorporated by reference.

Plasmid pDCQ330 was used to confirm the carotenoid hydroxylase activity of the novel genes. It contained the crtEidiYIB gene cluster isolated from *P. agglomerans* DC404. Isolation of the carotenoid gene cluster from *Pantoea agglomerans* strain DC404 and construction of plasmid pDCQ330 were previously described in U.S. Ser. No. 10/808,807; hereby incorporated by reference.

DC260 and DC404 were carotenoid-producing strains isolated from the environment in Wilmington, Del. *Enterobacteriaceae* strain DC260 was isolated from the surface of a brick on a west-facing wall of a residential house. *Pantoea agglomerans* strain DC404 was isolated from soil in a residential vegetable garden. Samples were washed and a 10-µL loopful of the resuspension was streaked onto Luria-Broth (LB) plates and the plates were incubated at 30° C. Pigmented bacteria with diverse colony appearances were picked and streaked twice to homogeneity on LB plates and incubated at 30° C. From these colonies, DC260 and DC404 were isolated which formed pale yellow smooth translucent colonies.

Cosmid library was constructed for DC260 and DC404 to clone β-carotene synthesis gene clusters using the pWEB cosmid cloning kit from Epicentre (Madison, Wis.) following the manufacturer's instructions. Genomic DNA was sheared by passing it through a syringe needle. The sheared DNA was end-repaired and size-selected on low-melting-point agarose by comparison with a 40 kB standard. DNA fragments approximately 40 kB in size were purified and ligated into the blunt-ended cloning-ready pWEB cosmid vector. The library was packaged using ultra-high efficiency MaxPlax™ Lambda Packaging Extracts (Epicentre Technologies, Madison, Wis.), and plated on EPI100 *E.coli* cells. Two yellow colonies were identified from each of the cosmid libraries and referred to herein as pWEB-260 (containing the crtEXYIBZ gene cluster; SEQ ID NO: 6) and pWEB-404.

The carotenoid gene clusters on the two cosmids were sequenced and subcloned onto pBHR1 vector (MoBiTec, Goettingen, Germany). Primers pWEB260F: 5'-GAAT-TCACCAACCATGGATAGCCATTATGAC-3' (SEQ ID NO: 7) and pWEB260R: 5'-GAATTCAACGAGGACGCT-GCCACAGA-3' (SEQ ID NO: 8) were used to amplify a fragment containing the crtEXYIB genes from pWEB-260. Primers pWEB404F: 5'-GAATTCACTAGTCGAGACGC-CGGGTACCAACCAT-3' (SEQ ID NO: 9) and pWEB404R: 5'-GAATTCTAGCGCGGGCGCTGCCAGA-3' (SEQ ID NO: 10) were used to amplify a fragment containing the crtEidiYIB genes (SEQ ID NO: 11) from pWEB-404. Pfu Turbo polymerase (Stratagene, La Jolla, Calif.) was used for the PCR with the following thermocycler conditions: 92° C. (5 min); 94° C. (1 min), 60° C. (1 min), 72° C. (9 min) for 25 cycles; and 72° C. (10 min). Taq polymerase (Perkin Elmer) was used in a ten minute 72° C. reaction to add additional 3' adenosine nucleotides to the fragment for TOPO® cloning into pTrcHis2-TOPO® (Invitrogen, Carlsbad, Calif.). Following transformation to *E. coli* TOP10 cells, several colonies appeared yellow in color, indicating that they were producing a carotenoid compound. The gene cluster was then subcloned into the broad host range vector pBHR1 and electroporated into *E. coli* 10G cells (Lucigen, Middletown, Wis.). The transformants containing the respective resulting plasmid, either pDCQ329 or pDCQ330, were selected on LB medium containing 50 μg/mL kanamycin. They were confirmed by restriction digests and shown to produce β-carotene.

Example 3

Isolation of Carotenoid Ketolase Genes from *Brevundimonas vesicularis* DC263 and *Sphinqomonas melonis* DC18

This example describes construction of the small insert library from the bacterial strains *Brevundimonas vesicularis* DC263 and *Sphingomonas melonis* DC18 and cloning of the ketolase gene from each strain (see U.S. Ser. No. 11/015, 433).

Library Construction and Screening

Cells of DC263 and DC18 were grown as described in Example 1. Genomic DNA was prepared from the cells using the Qiagen genomic DNA preparation kits. The small insert library of strain DC263 and DC18 was prepared by random shearing method. Genomic DNA of DC263 and DC18 was sheared by passing through a 291/2 G insulin syringe (Becton Dickinson, Franklin Lakes, N.J.) about 300 times and separated on a 0.8% agarose gel. The 4–6 kb fraction was excised from the gel and extracted using Qiagen MinElute™ Gel-Extraction kit (Qiagen). The ends of the extracted DNA were repaired using Lucigen DNA-Terminator® Repair kit. The repaired DNA inserts were ligated to pEZseq™ vector using pEZSeq™ Blunt Cloning kit (Lucigen). The ligation mixture was electroporated into freshly prepared competent cells of *E. coli* 10G containing a β-carotene producing plasmid pDCQ329 (U.S. Ser. No. 10/808,979). Transformants were plated on LB plates with 100 μg/mL ampicillin and 50 μg/mL kanamycin. Approximately 50,000 to 100,000 transformants were obtained for each library. Several orange colonies were identified among the tens of thousands of yellow colonies for each library. These positive clones were identified as possibly containing a ketolase gene that converted β-carotene to ketocarotenoids.

Isolation of Carotenoid Ketolase Genes

The pEZ-based plasmid was separated from the β-carotene reporter plasmid by selecting for ampicillin resistant and kanamycin sensitive clones. The insert on the pEZ-based plasmid was sequenced by random transposon insertion using the EZ-TN<TET-1> kit (Epicentre, Madison, Wis.) and/or primer walking. The sequences were assembles with the Sequencher™ program (Gene Codes Corp., Ann Arbor, Mich.). Genes encoding CrtW ketolases were identified by conducting BLAST (Basic Local Alignment Search Tool; Altschul, S. F., et al., *J. Mol. Biol.* 215:403–410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The coding sequences of the crtW genes from *Brevundimonas vesicularis* DC263 and *Sphingomonas melonis* DC18 were listed as SEQ ID NO: 12 and SEQ ID NO: 13, respectively.

Example 4

Isolation of Carotenoid Hydroxylase Genes

This example describes isolation of carotenoid hydroxylase genes from two bacterial strains, *Brevundimonas vesicularis* DC263 and *Novosphingobium aromaticivorans* ATCC No. 700278 (previously named *Sphingomonas aromaticivorans*).

Isolation of Carotenoid Hydroxylase Gene from *Brevundimonas vesicularis* DC263

The pEZ-based plasmid containing the crtW gene (SEQ ID NO: 12) from DC263 was sequenced and the carotenoid hydroxylase gene was not identified on the 3 kb insert of the pEZ-based plasmid. In order to sequence more of the flanking region, cosmid library was constructed as described earlier for DC263 using the pWEB cosmid cloning kit from Epicentre (Madison, Wis.) following the manufacturer's instructions. Approximately 600 cosmid clones were grown in 100 μL LB containing 100 μg/mL ampicillin in microtiter plates. The plates were incubated at 30° C. with shaking at 700 rpm for 24 hours. The cosmid library was screened by PCR using primers pEZ263-F: 5'-GTTCGAACTGGG-GAAAACGGAC-3' (SEQ ID NO: 14) and pEZ263-R: 5'-CAAAGGCGTGAACCGAAATCCG-3' (SEQ ID NO: 15) designed around the crtW region of the pEZ-based plasmid. A positive cosmid clone F3-4 was isolated containing an approximately 40 kb insert extending the crtW region. The cosmid DNA was prepared and sequenced by random transposon insertion using the EZ-TN<TET-1> kit (Epicentre, Madison, Wis.) and/or primer walking. The sequences were assembles with the Sequencher™ program v 4.05 (Gene Codes Corp., Ann Arbor, Mich.).

The crtZ hydroxylase gene coding sequence (SEQ ID NOs: 16) was identified by conducting BLAST (Basic Local Alignment Search Tool; Altschul, S. F., et al., *J. Mol. Biol.* 215:403–410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequence was analyzed for similarity to all publicly available DNA sequences contained in the "nr" database using the BLASTN algorithm provided by the National Center for Biotechnology Information (NCBI). DNA sequence was translated in all reading frames and compared for similarity to all publicly available protein sequences contained in the "nr" database using the BLASTX algorithm (Gish, W. and States, D. J., *Nature Genetics*, 3:266–272 (1993)) provided by the NCBI. BLAST analysis identified an ORF that shared homology to β-carotene hydroxylases. The top hit was to a β-carotene hydroxylase from *Alcaligenes* sp. (GenBank® accession number Q44262) with 51% amino acid identity. Table 3 displays data based on the BLASTXnr algorithm with values reported in expect values.

The crtW-containing cosmid of *Sphingomonas melonis* DC18 was also isolated and sequenced similarly as described above for *Brevundimonas vesicularis* DC263. However, the crtZ hydroxylase gene of DC18 was not found in the cosmid containing *Sphingomonas melonis* DC18 crtW.

Isolation of Carotenoid Hydroxylase Gene from *Novosphingobium aromaticivorans* ATCC 700278

To identify more carotenoid hydroxylase genes, the partial genome sequence database of *Novosphingobium aromaticivorans* ATCC No. 700278 was searched. The β-carotene hydroxylase (CrtZ) from *Agrobacterium aurantiacum* (SEQ ID NO: 18) was used to BLAST the genome database of *Novosphingobium aromaticivorans*. A hypothetical protein from *Novosphingobium aromaticivorans* (GenBank® protein Accession No. ZP_00094836.1; SEQ ID NOs. 19 and 20) was identified that exhibited 52% amino acid identity with the *Agrobacterium* CrtZ. This hypothetical protein was then used to BLAST the nr databases. The top hit was 57% identity to the CrtZ from *Pantoea agglomerans* pv. *Milletiae*. The vast majority of the other "hits" from the BLAST analysis were to β-carotene hydroxylases from different organisms. The hypothetical protein from *Novosphingobium aromaticivorans* was assayed for β-carotene hydroxylase activity.

The nucleotide and amino acid sequences of the two CrtZ carotenoid hydroxylases identified here were also compared with several known carotenoid hydroxylase genes using multiple sequence alignment algorithms in Vector NTI. Table 4 displays the percentage of nucleotide sequence identity and amino acid sequence identity for the pairwise comparisons. The two crtZ genes isolated share only low to moderate homology with the known crtZ genes and are also very divergent from each other.

TABLE 3

Top BLAST Hits for the Carotenoid Hydroxylase Genes Isolated from Different Bacterial Species

| ORF | Gene Name | Similarity Identified | SEQ ID Nucleotide | SEQ ID Peptide | % Identity[a] | % Similarity[b] | E-value[c] | Citation |
|---|---|---|---|---|---|---|---|---|
| 1 | crtZ_*Brevundimonas vesicularis* DC263 | beta-carotene hydroxylase gi\|2498258\|sp\|Q44262\|CRTZ_ALC SP [*Alcaligenes* sp] | 17 | 18 | 51 | 67 | 3e-33 | Misawa, et al., Biochem. Biophys. Res. Commun. 209 (3), 867–876 (1995) |
| 2 | crtZ_*Novosphingobium aromaticivorans* ATCC 700278 | beta-carotene hydroxylase gi\|18143450\|dbj\|BAB79605.1\| CrtZ [*Pantoea agglomerans* pv. *milletiae*] | 20 | 21 | 57 | 73 | 3e-39 | Kamiunten, et al., unpublished (2001) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

TABLE 4

Pairwise Comparison of the Nucleotide and Amino Acid Sequences of the β-carotene Hydroxylases.

| DNA/AA Identity[a] | *Brevundimonas vesicularis* | *Novosphingobium aromaticivorans* | *Pantoea agglomerans* pv. *milletiae* | *Flavobacterium* sp. | *Pantoea ananatis* | *Alcaligenes* sp. | *Agrobacterium aurantiacum* |
|---|---|---|---|---|---|---|---|
| *Brevundimonas vesicularis* | 100/100 | 60/45 | 52/49 | 56/50 | 50/48 | 59/52 | 61/51 |
| *Novosphingobium aromaticivorans*[b] | | 100/100 | 52/49 | 57/49 | 53/49 | 57/49 | 57/46 |
| *Pantoea agglomerans* pv. *milletiae*[c] | | | 100/100 | 54/52 | 81/87 | 59/56 | 57/54 |
| *Flavobacterium* sp.[d] | | | | 100/100 | 52/49 | 71/69 | 73/67 |
| *Pantoea ananatis*[e] | | | | | 100/100 | 57/54 | 59/54 |
| *Alcaligenes* sp.[f] | | | | | | 100/100 | 85/90 |
| *Agrobacterium aurantiacum*[g] | | | | | | | 100/100 |

[a]Percentage of nucleotide sequence identity and amino acid sequence identity.
[b]*Novosphingobium aromaticivorans*, accession AAAV01000142.1
[c]*Pantoea agglomerans* pv. *milletiae*, accession BAB79605
[d]*Flavobacterium* sp., accession AAC44852
[e]*Pantoea ananatis*, GenBank ® accession D90087
[f]*Alcaligenes* sp, SwissProt accession Q44262
[g]*Agrobacterium aurantiacum*, SwissProt accession P54973

Example 5

Confirmation of the Carotenoid Hydroxylase Function

This example describes expression of the novel carotenoid hydroxylase genes in an *E. coli* strain producing β-carotene. Function of each hydroxylase gene was demonstrated by conversion of β-carotene to zeaxanthin.

Figure 3:
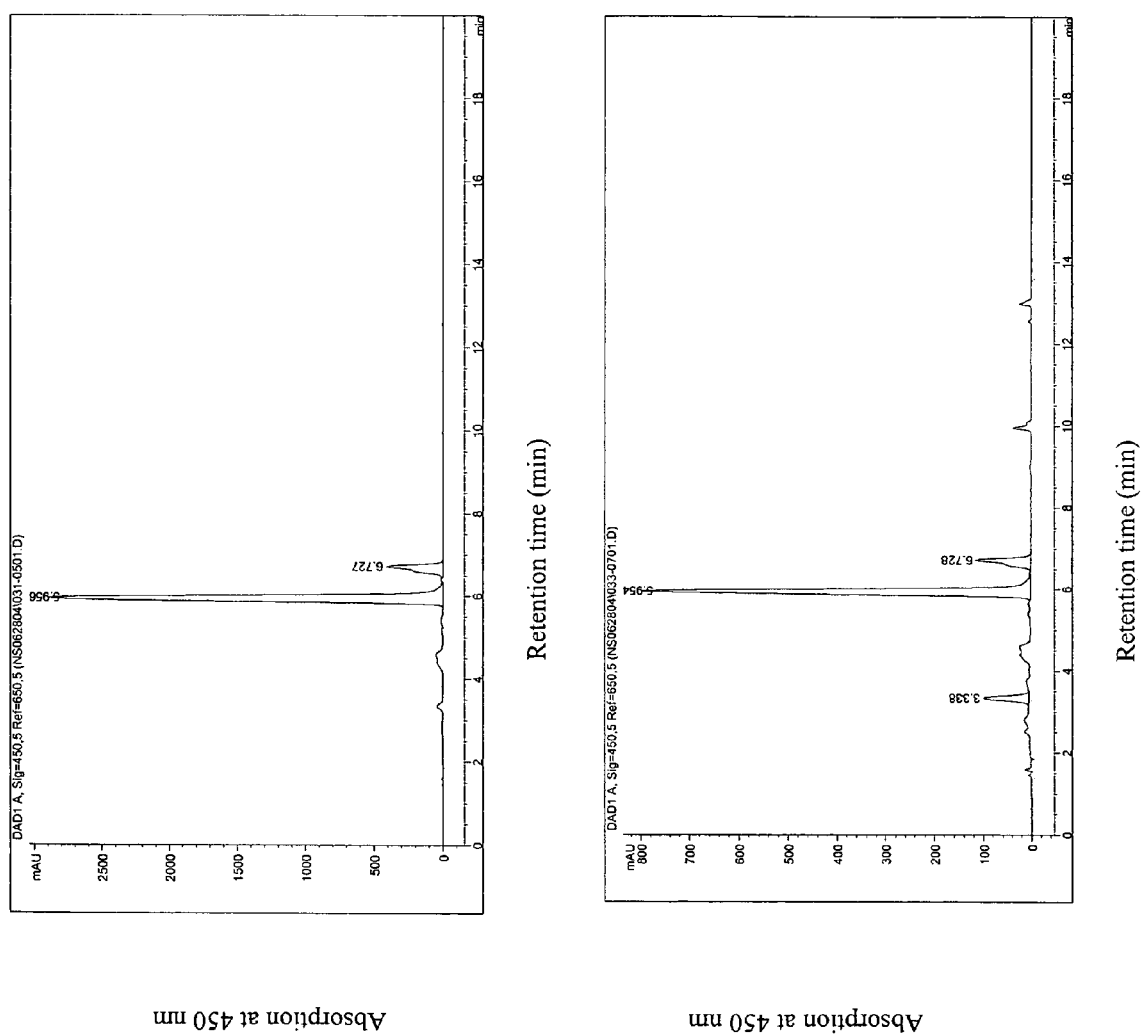
FIG. 3 shows the HPLC analysis of carotenoids produced by zeaxanthin producing *E.coli* strains expressing the crtZ gene from *Brevundimonas vesicularis* DC263 or *Novosphingobium aromaticivorans* ATCC No. 700278.

The β-carotene producing strain used in this study was the *E. coli* strain containing plasmid pDCQ330. The putative hydroxylase genes from the two bacterial strains were amplified by PCR. The crtZ from *Brevundimonas vesicularis* DC263 was amplified using primers crtZ-DC263_F: 5'-ACTAGTAAGGAGGAATAAACCATGTC-CTGGCCGACGATGATC' (SEQ ID NO: 21) and crtZ-DC263_R: 5'-TAGATCAGGCGCCGTTGCTGGATGA-3' (SEQ ID NO: 22). The crtZ from ATCC 700278 was amplified using primers 41ZSPH_F: 5'-ACTAGTTCTA-GATAAGGAGGAATAAACCATGCA-GACGCTTGCCGCG-3' (SEQ ID NO: 23) and SPH_ZR: 5'-GCTAGCCCTAGGTTAGCCGTCCACTGCCTC-3' (SEQ ID NO: 24). The PCR products were cloned into pTrcHis2-TOPO® (Invitrogen) vector and screened for clones containing the insert in the forward orientation. These resulted in pDCQ370TA expressing the crtZ gene from DC263, and pTrcHis2-ZS(Sphingo) expressing the crtZ gene from *Novosphingobium aromaticivorans* ATCC No. 700278. These constructs were transformed into the β-carotene accumulating *E. coli* strain containing pDCQ330. The carotenoids in the transformants were analyzed by HPLC (FIG. 3) as described in Example 1. The predominant peak eluted at 5.96 min had absorption spectra of (456 nm, 480 nm) and molecular weight m/z of 569, which were identical to those of the zeaxanthin synthetic standard. The zeaxanthin standard was purchased from CaroteNature (Lupsingen, Switzerland). Synthesis of zeaxanthin clearly demonstrated the hydroxylase function of the two new crtZ genes.

Example 6

Cloning of Astaxanthin-Producing Plasmids

This example describes construction of astaxanthin-producing plasmids by expressing the crtZ genes from *Brevundimonas vesicularis* DC263 or *Novosphingobium aromaticivorans* ATCC No. 700278 with a crtW gene and a β-carotene synthesis gene cluster.

Cloning of an Astaxanthin-Producing Plasmid Containing crtZ from *Brevundimonas vesicularis* DC263

First, the β-carotene synthesis gene cluster crtEYIB was constructed from pDCQ329 by removing the crtX gene. To facilitate subsequent cloning, the EcoRI site at the end of crtY gene was also removed. The primers crt-260_F: 5'-GAATTCACTAGTACCAACCATGGATAGC-CATTATG-3' (SEQ ID NO: 25) and crt-260SOE_R: 5'-AT-CAGGTCGCCTCCGCCAGCAC-GACTTTCAGTTGAATATCGCTAGCTGTTG-3' (SEQ ID NO: 26) were used to amplify the crtE gene. The primers crt-260SOE_F: 5'-CAACAGCTAGCGATATTCAACT-GAAAGTCGTGCTGGCGGAGGCGACCTGAT-3' (SEQ ID NO: 27) and crt-260RI_R: 5'-CATTTTTTCTTCCCTG-GTTCGACAGAGTTCAACAGCGCGCGCAGCGCTT-3' (SEQ ID NO: 28) were used to amplify the crtY gene. The AAT codon in the EcoRI site was replaced with an alternative AAC codon to remove the EcoRI site. The crtEY genes were linked together by a SOEing PCR using primers crt-260_F and crt-260RI_R. The crtIB fragment was amplified with primers crt-260RI_F: 5'-AAGCGCT-GCGCGCGCTGTTGAACTCTGTCGAAC-CAGGGAAGAAAAAATG-3' (SEQ ID NO: 29) and crt-260_R: 5'-GAATTCAACGAGGACGCTGCCACAGA-3' (SEQ ID NO: 30). The crtEYIB genes were linked together by another SOEing PCR using primers crt-260_F and crt-260_R. The 4.5 kb EcoRI fragment containing the crtEYIB genes was cloned into the EcoRI site of pBHR1, resulting pDCQ340. *E. coli* containing pDCQ340 was shown to produce β-carotene.

The crtW and crtZ genes from DC263 were then cloned upstream of the crtEYIB cluster on pDCQ340. The crtW from DC263 was amplified using primers crtW-263_F: 5'-ACTAGTAAGGAGGAATAAACCATGCG-GCAAGCGAACAGGATG-3' (SEQ ID NO: 31) and crtW-263_R: 5'-TCTAGACTAGCTGAACAAACTCCACCAG-3' (SEQ ID NO: 32). The crtZ from DC263 was amplified using primers crtZ-263_F2: 5'-TCTAGAAAGGAG-GAATAAACCATGTCCTGGCCGACGATGATC-3' (SEQ ID NO: 33) and crtZ-263_R2: 5'-ACTAGTCAGGCGC-CGTTGCTGGATGA-3' (SEQ ID NO: 34). The PCR products were cloned into pTrcHis2-TOPO® vector resulting pDCQ342TA and pDCQ352, respectively. The 0.8 kb SpeI-XbaI fragment from pDCQ342TA containing the crtW was cloned into the SpeI site of pDCQ340. The resulted pDCQ342 contained the crtW upstream of crtEYIB gene cluster. The 0.5 kb XbaI-SpeI fragment from pDCQ352 containing crtZ was then cloned into the SpeI site upstream of the crtW on pDCQ342. This resulted in an astaxanthin-producing plasmid, pDCQ344, which contained the crtZWEYIB gene cluster expressed from the chloramphenicol resistance gene promoter (Pcat) on the pBHR1 vector.

Cloning of an Astaxanthin-Producing Plasmid Containing crtZ from *Novosphingobium aromaticivorans* ATCC No. 700278

The crtZ from *Novosphingobium aromaticivorans* was co-expressed with the crtW from *Sphingomonas melonis* DC18 under an endogenous *Methylomonas* promoter, Phps1 (U.S. Ser. No. 10/689,200; hereby incorporated by reference). The Phps1 promoter was amplified from *Methylomonas* 16a genomic DNA using the upstream primer 5'-CCATGGGCTAGCTAAGGATTGGGGTGCGT-3' (SEQ ID NO: 35) and the downstream primer 5'-CCATGGAC-TAGTGTGATGTGCTCCGAAAGT-3' (SEQ ID NO: 36). The 288 bp NcoI fragment containing Phps1 was cloned into the NcoI site of pBHR1 resulting pDCQ363. The crtZ from *Novosphingobium aromaticivorans* ATCC No. 700278 was digested with SpeI and NheI from pTrcHis2-ZS(Sphingo) and cloned into the SpeI site of pDCQ363 resulting pDCQ364. The crtW from *Sphingomonas melonis* DC18 was amplified using primers crtW_sphingo_F 5'-ACTAG-TAAGGAGGAATAAACCATGACCGTCG-3' (SEQ ID NO: 37) and crtW_sphingo_R 5'-ATCTAGATTACCG-GTCTTTGCTTAACGACCG-3' (SEQ ID NO: 38). The SpeI-XbaI fragment containing the crtW was cloned into the SpeI and XbaI sites of pDCQ364. In the resulted construct pDCQ365, the crtW from *Sphingomonas melonis* DC18 and the crtZ from *Novosphingobium aromaticivorans* ATCC No. 700278 were co-expressed as one transcriptional unit under the endogenous *Methylomonas* promoter Phps1. The NcoI fragment containing this crtWZ transcriptional unit was then cloned into the NcoI site of a β-carotene synthesis plasmid pDCQ330 resulting in the astaxanthin-producing plasmid pDCQ366.

Example 7

Production of Astaxanthin in *E. coli* and *Methylomonas*

This example describes the process used to transform the astaxanthin-producing plasmids into two unrelated microbial host cells, such as *E. coli* and *Methylomonas* sp. 16a (ATCC PTA-2402), to produce astaxanthin based on previously reported methods (U.S. Ser. No. 10/997,844; hereby incorporated by reference).

Briefly, the plasmids were transferred into *Methylomonas* 16a by triparental conjugal mating (U.S. Ser. No. 10/997,844). An *E. coli* helper strain containing pRK2013 (ATCC No. 37159) and the *E. coli* 10G or DH10B donor strain containing the plasmid pDCQ344 or pDCQ366 were grown overnight in LB medium containing kanamycin (50 µg/mL), washed three times in LB, and resuspended in a volume of LB representing approximately a 60-fold concentration of the original culture volume.

The *Methylomonas* sp. 16a MWM1200 strain contains a double crossover knockout of the crtN1aldcrtN2 gene cluster, which disrupted the synthesis of the native $C_{30}$ carotenoids (U.S. Ser. No. 10/997,844). (The MWM1200 strain was grown as the recipient using the general conditions described in U.S. Ser. No. 09/941,947. Briefly, *Methylomonas* 16a MWM1200 strain was grown in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking.

Nitrate Medium for *Methylomonas* 16A

Nitrate liquid medium, also referred to herein as "defined medium" or "BTZ-3" medium is comprised of various salts mixed with Solution 1 as indicated below (Tables 5 and 6) or where specified the nitrate is replaced with 15 mM ammonium chloride. Solution 1 provides the composition for 100-fold concentrated stock solution of trace minerals.

TABLE 5

Solution 1*

| | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 6

Nitrate liquid medium (BTZ-3)**

| | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |

TABLE 6-continued

Nitrate liquid medium (BTZ-3)**

| | MW | Conc. (mM) | g per L |
|---|---|---|---|
| $CaCl_2 \times 2H_2O$ | 147.02 | 0.68 | 0.1 |
| 1 M HEPES (pH 7) | 238.3 | | 50 mL |
| Solution 1 | | | 10 mL |

**Dissolve in 900 mL $H_2O$. Adjust to pH = 7, and add $H_2O$ to give 1 L. For agar plates: Add 15 g of agarose in 1 L of medium, autoclave, let cool down to 50° C., mix, and pour plates.

The standard gas phase for cultivation contains 25% methane in air. The *Methylomonas* sp. 16a MWM1200 recipient strain was cultured under these conditions for 48 h in BTZ-3 medium, washed three times in BTZ-3, and resuspended in a volume of BTZ-3 representing a 150-fold concentration of the original culture volume.

The donor, helper, and recipient cell pastes were combined in ratios of 1:1:2, respectively, on the surface of BTZ-3 agar plates containing 0.5% (w/v) yeast extract. Plates were maintained at 30° C. in 25% methane for 16–72 hours to allow conjugation to occur, after which the cell pastes were collected and resuspended in BTZ-3. Dilutions were plated on BTZ-3 agar containing kanamycin (50 µg/mL) and incubated at 30° C. in 25% methane for up to 1 week. Orange-red transconjugants were streaked onto BTZ-3 agar with kanamycin (50 µg/mL).

For analysis of carotenoid composition, *Methylomonas* transconjugants were cultured in a 24-well block (Qiagen) with each well containing 1 mL BTZ-3 containing kanamycin (50 µg/mL). The block was covered with Airpore™ film (Qiagen) and incubated in an AnaeroPack™ System (Mitsubishi Gas Chemical Co., Inc., Japan) filled with 25% methane as the sole carbon source. The AnaeroPack™ was shaking at 250 rpm for 2–3 days at 30° C. *E. coli* cells containing the astaxanthin plasmid was grown in 25 ml LB containing kanamycin (50 µg/mL) at 30° C. shaking at 250 rpm for 2–3 days. The cells were harvested by centrifugation and the pellets were extracted and carotenoid content was analyzed by HPLC, as described in Example 1.

Figure 4:
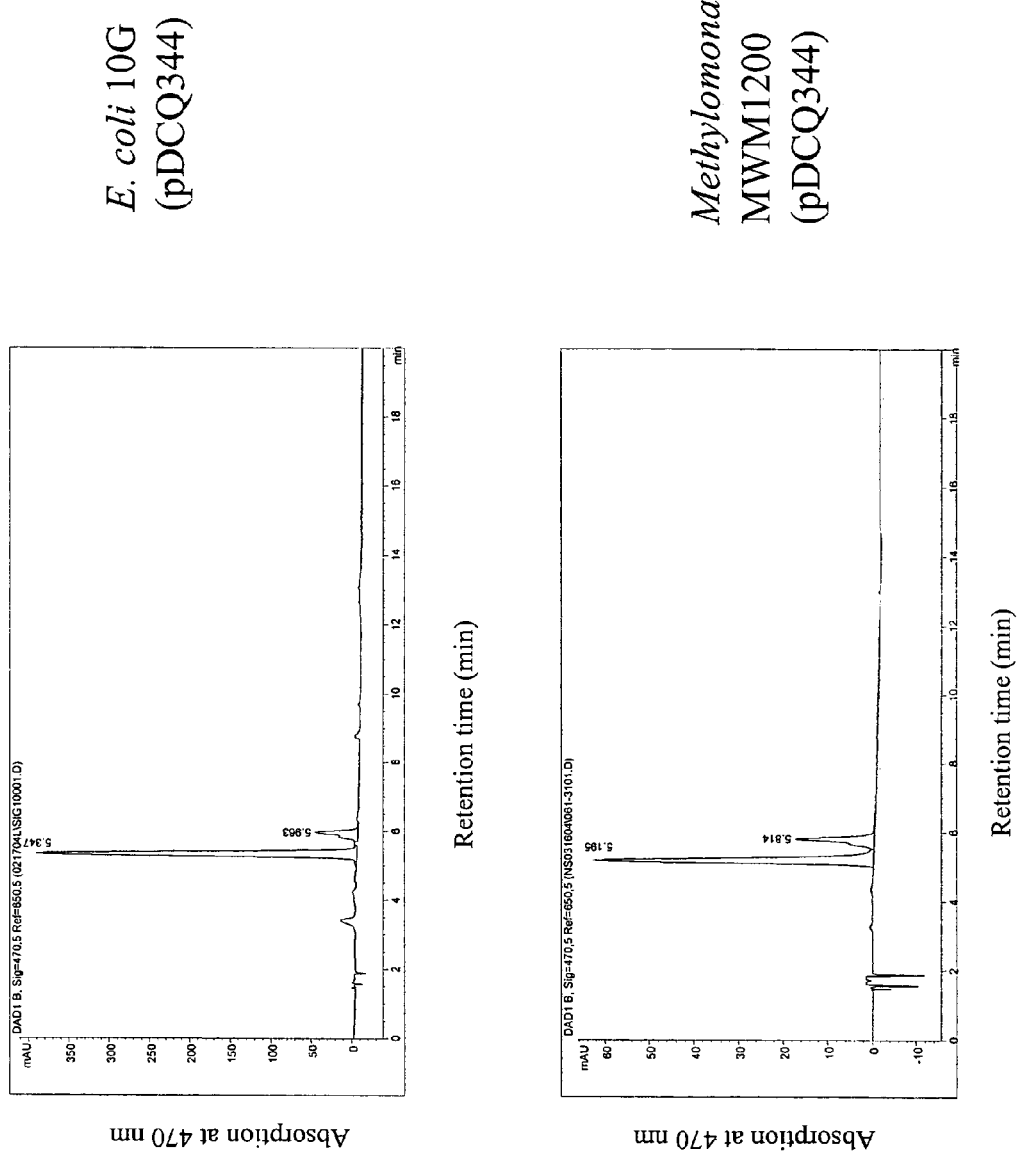
FIG. 4 shows the HPLC analysis of carotenoids produced by astaxanthin producing *E. coli* and *Methylomonas* sp. 16a strains expressing the crtZ gene from *Brevundimonas vesicularis* DC263.
Figure 5:
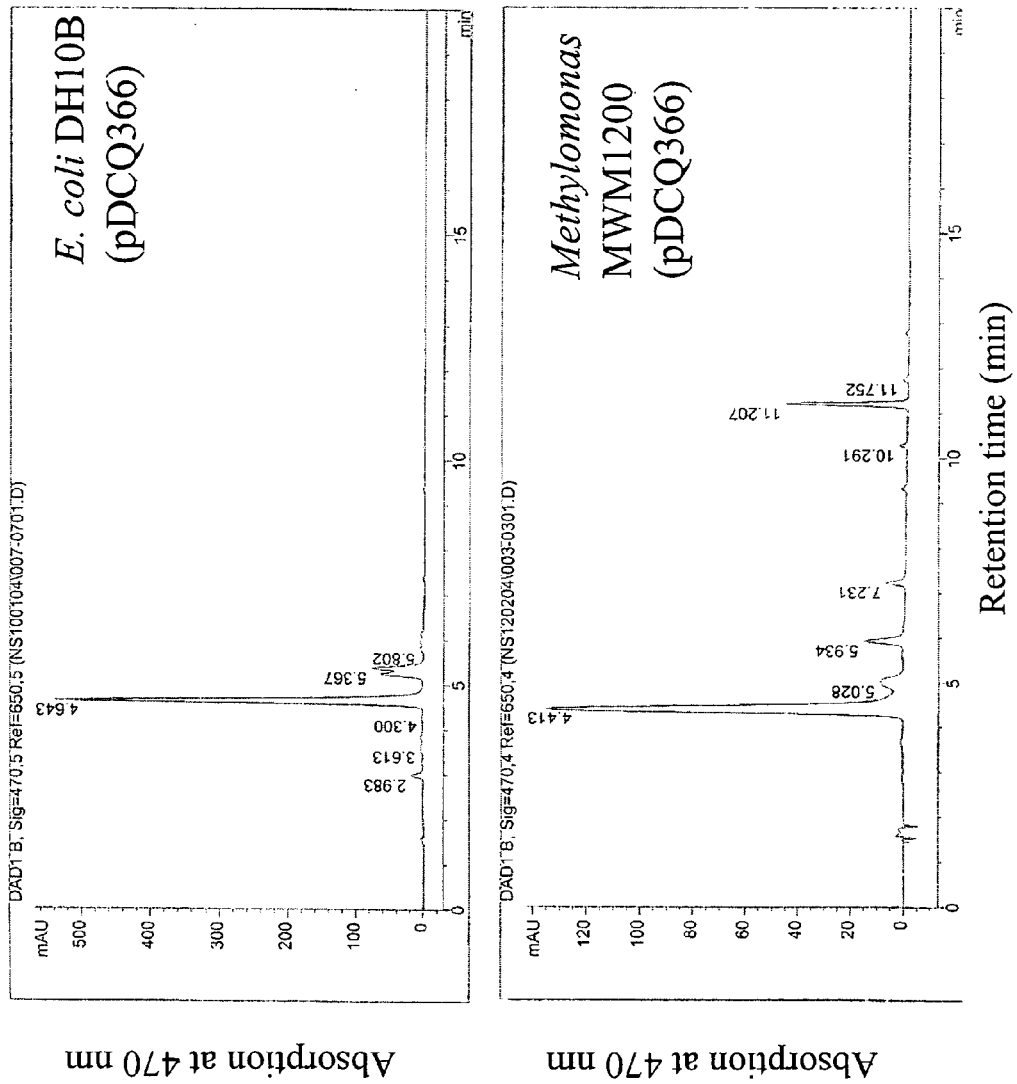
FIG. 5 shows the HPLC analysis of carotenoids produced by astaxanthin producing *E. coli* and *Methylomonas* sp. 16a strains expressing the crtZ gene from *Novosphingobium aromaticivorans* ATCC No. 700278.

HPLC analysis of extracts from *E. coli* 10G or *Methylomonas* 16a MWM1200 containing pDCQ344 was shown in FIG. 4. Astaxanthin comprised of approximately 80% of total carotenoids produced in *E. coli* or *Methylomonas* containing pDCQ344. The astaxanthin peak eluted at 5.2–5.3 min had absorption maximum of 480 nm and molecular weight m/z of 597, which were identical to those of the synthetic standard of astaxanthin. The minor peak eluted at 5.8–5.9 min had absorption maximum of 464 nm and molecular weight m/z of 583, which were identical to those of the synthetic standard of adonixanthin. The synthetic astaxanthin and adonixanthin standards were purchased from CaroteNature (Lupsingen, Switzerland). HPLC analysis of extracts from *E. coli* DH10B or *Methylomonas* 16a MWM1200 containing pDCQ366 was shown in FIG. 5. Astaxanthin was produced from both the *E. coli* and the *Methylomonas* as the predominant carotenoid eluted at 4.4–4.6 min in this run. In addition to several minor peaks, a peak eluted at 11.2 min comprised of 10% of total carotenoids in *Methylomonas*. This peak had absorption maximum of 448 nm, 474 nm, 504 nm and molecular weight m/z of 536, which agrees with those for lycopene, an intermediate for astaxanthin biosynthesis.

What is claimed is:

1. An isolated nucleic acid molecule encoding a carotenoid hydroxylase enzyme selected from the group consisting of:
   (a) an isolated nucleic acid molecule encoding an amino acid as set forth in SEQ ID NO: 17;
   (b) an isolated nucleic acid molecule comprising a first nucleotide sequence encoding a carotenoid hydroxylase enzyme having at least 95% identity to a polypeptide comprised of an amino acid sequence as represented by SEQ ID NO: 17;
   (c) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; and
   (d) an isolated nucleic acid molecule that is complementary to (a), (b), or (c).

2. An isolated nucleic acid molecule according to claim 1 as represented by SEQ ID NO:16.

3. A chimeric genetic construct comprising the isolated nucleic acid molecule of claim 1 or 2 operably linked to suitable regulatory sequences.

4. A transformed host cell comprising an isolated nucleic acid molecule according to claim 1.

5. The transformed host cell of claim 4 wherein the host cell is selected from the group consisting of bacteria, yeast, filamentous fungi, algae, and green plants.

6. The transformed host cell of claim 5 wherein the host cell is selected from the group consisting of *Aspergillus, Trichoderma, Saccharomyces, Pichia, Candida, Hansenula, Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium,*

*Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

7. The transformed host cell of claim 5 wherein the host cell is selected from the group consisting of soybean, rapeseed, sunflower, cotton, corn, tobacco, alfalfa, wheat, barley, oats, sorghum, rice, *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

* * * * *